US009181558B2

(12) United States Patent
Roessler et al.

(10) Patent No.: US 9,181,558 B2
(45) Date of Patent: Nov. 10, 2015

(54) PRODUCTION OF BRANCHED-CHAIN ALCOHOLS BY PHOTOSYNTHETIC MICROORGANISMS

(71) Applicant: Synthetic Genomics, Inc., La Jolla, CA (US)

(72) Inventors: Paul Gordon Roessler, San Diego, CA (US); Bo Liu, San Diego, CA (US); Jessica Roxane Kristof, San Diego, CA (US)

(73) Assignee: Synthetic Genomics, Inc., La Jolla, CA (US)

(*) Notice: Subject to any disclaimer, the term of this patent is extended or adjusted under 35 U.S.C. 154(b) by 360 days.

(21) Appl. No.: 13/898,754

(22) Filed: May 21, 2013

(65) Prior Publication Data

US 2013/0316415 A1 Nov. 28, 2013

Related U.S. Application Data

(63) Continuation of application No. 13/338,579, filed on Dec. 28, 2011, now Pat. No. 8,445,257, which is a continuation of application No. 12/635,653, filed on Dec. 10, 2009, now Pat. No. 8,124,400.

(60) Provisional application No. 61/121,522, filed on Dec. 10, 2008.

(51) Int. Cl.
| | |
|---|---|
| C12N 15/82 | (2006.01) |
| C07C 31/12 | (2006.01) |
| C12N 15/52 | (2006.01) |
| C12P 7/04 | (2006.01) |
| C12P 7/16 | (2006.01) |
| C12N 15/74 | (2006.01) |

(52) U.S. Cl.
CPC ............ *C12N 15/82* (2013.01); *C07C 31/12* (2013.01); *C12N 15/52* (2013.01); *C12N 15/74* (2013.01); *C12P 7/04* (2013.01); *C12P 7/16* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 4,778,759 | A | 10/1988 | Szalay et al. |
| 6,455,284 | B1 | 9/2002 | Gokarn et al. |
| 7,855,061 | B2 | 12/2010 | Vance |
| 8,124,400 | B2 | 2/2012 | Roessler et al. |
| 2007/0092956 | A1 | 4/2007 | Rajgarhia et al. |
| 2007/0092957 | A1 | 4/2007 | Donaldson et al. |
| 2007/0117183 | A1 | 5/2007 | Pompejus et al. |
| 2007/0259411 | A1 | 11/2007 | Bramucci et al. |
| 2008/0081746 | A1 | 4/2008 | Woodruff et al. |
| 2008/0261230 | A1 | 10/2008 | Liao et al. |
| 2009/0081746 | A1 | 3/2009 | Liao et al. |
| 2009/0111154 | A1 | 4/2009 | Liao et al. |
| 2009/0288337 | A1 | 11/2009 | Picataggio et al. |
| 2010/0209986 | A1 | 8/2010 | Liao et al. |

FOREIGN PATENT DOCUMENTS

| | | |
|---|---|---|
| WO | WO 2007/136133 A1 | 11/2007 |
| WO | WO 2009/006429 A1 | 1/2009 |
| WO | WO 2009/076480 A2 | 6/2009 |
| WO | WO 2010/071851 A2 | 6/2010 |

OTHER PUBLICATIONS

Deng, M. et al. Applied and Environmental Microbiology, Feb. 1999, pp. 523-528.*
2,3-dihydroxy-3-methylbutanoate (Apr. 22, 2008) (CHEBI:49072).
2-acetyl-2-hydroxybutanoate (Chebi:49256). Last modified on May 8, 2008. Retrieved from the Internet on Jan. 29, 2010: http://www.ebi.ac.uk/chebi/advancedSearchFT.do?searchString=2-hydroxy-2-e-thy-3-oxobutanoate] cited to demonstrate equivalence of chemical species of alternate nomenclature.
Atsumi et al., "Non-fermentative pathways for synthesis of branched-chain higher alcohols as biofuels", *Nature*, 451(7174):86-90 +suppl page (2008).
Atsumi et al., "Direct photosynthetic recycling of carbon dioxide to isobutyraldehyde"; *Nature Biotechnology;* Advance Online Publication; 1-4; published online Nov. 15, 2009.
Burkovski, "Bacterial amino acid transport proteins: occurrence, functions, and significance for biotechnological applications", *Appl. Microbiol. Biotechnol.*, 58(3):265-274 (2002).
Cann and Liao, "Production of 2-methyl-1-butanol in engineered *Escherichia coli*", *Appl. Microbiol. Biotechnol.*, 81(1):89-98 (2008).
Deng and Coleman, "Ethanol synthesis by genetic engineering in cyanobacteria", *Applied and Environmental Microbiology*, 65(2):523-528 (1999).
Dickinson et al., "The Catabolism of Amino Acids to Long Chain and Complex Alcohols in Saccharomyces cerevisiae", *J. Biol. Chem.*, 278(10):8028-8034 (2003).
Kutter et al., "The crystal structure of pyruvate decarboxylase from Kluyveromyces lactis. Implications for the substrate activation mechanism of this enzyme", *FEBS J.*, 273(18):4199-4209 (2006).
Labarre et al., "Genetic Analysis of Amino Acid Transport in the Facultatively Heterotrophic *Cyanobacterium cynechocystis* sp. Strain 6803", *J. Bacteriol.*, 169:4668-4673 (1987).
Larroy et al., "Characterization of a Saccharomyces cerevisiae NADP(H)-dependent alcohol dehydrogenase (ADHVII), a member of the cinnamyl alcohol dehydrogenase family", *Eur. J. Biochem.*, 269(22):5738-5745 (2002).
Maestri-El Kohen, "Biosynthesis of the Branched-Chain Amino Acids in the Cyanobacterium synechocystis PCC6803: Existence of Compensatory Pathways", *Current Microbiology*, 45:94-98 (2002).

(Continued)

*Primary Examiner* — Russell Kallis
(74) *Attorney, Agent, or Firm* — DLA Piper LLP (US)

(57) ABSTRACT

The present invention provides genes, polypeptides and expression constructs therefor, recombinant photosynthetic microorganisms, and method of use thereof, such as for the production of branched-chain alcohols (including 2-methyl-1-butanol, 3-methyl-1-butanol, and isobutanol) and derivatives thereof for a variety of uses.

25 Claims, 7 Drawing Sheets

(56) References Cited

OTHER PUBLICATIONS

Paulsen et al., "Microbial genome analyses: global comparisons of transport capabilities based on phylogenies, bioenergetics and substrate specificities", *J. Mol. Biol.*, 277(3):573-592 (1998).

Pohl et al., "Active site mutants of pyruvate decarboxylase from Zymomonas mobiliis", *Eur. J. Biochem.*, 257:538-546 (1998).

Risso et al., "Elucidation of an Alternative Isoleucine Biosynthesis Pathway in Geobacter sulfurreducens", *J. Bacteriol.*, 190:2266-2274 (2008).

Sakura et al., "A distinct type of alcohol dehydrogenase, adh4+, complements ethanol fermentation in an adh1-deficient strain of Schizosaccharomyces pombe", *FEMS Yeast Res.*, 4(6):649-654 (2004).

Sardessai and Bhosle, "Tolerance of bacteria to organic solvents", Research in Microbiology 153(5):263-268 (2002).

Atsumi et al., "Direct photosynthetic recycling of carbon dioxide to isobutyraldehyde", *Nat Biotechnol.*, 27(12):1177-80 (2009).

European Search Report (ESR) from application No. EP 09 83 2579, Jun. 27, 2013.

\* cited by examiner

ACTAGTTGTTGACAATTAATCATCCGGCTCGTATAATGTGTGGAATTGTGAGCGGATAACAATTTCACAC
AGGAAACAGACCATGGCTGAAATCACGCTGGGAAAATATCTGTTTGAACGGTTGAAGCAAGTCAATGTGA
ACACCGTGTTTGGCCTGCCTGGGGATTTCAACTTGAGTCTGTTGGACAAAATCTATGAAGTGGAAGGCAT
GCGATGGGCCGGTAACGCGAATGAGTTGAATGCGCGTTATGCTGCTGATGGTTACGCACGAATCAAGGGA
ATGAGCTGTATTATTACTACATTCGGTGTCGGCGAGCTGAGCGCATTGAATGGCATTGCTGGTTCCTACG
CAGAACATGTGGGGGTTCTCCATGTGGTGGGGGTGCCAAGCATCTCCAGCCAGGCGAAGCAATTGCTCCT
CCACCACACCTTGGGTAACGGGGATTTTACCGTCTTCCACCGGATGTCGGCAAATATCTCTGAGACAACG
GCCATGATCACTGATATTTGCACCGCGCCAGCCGAAATCGATCGGTGTATCCGTACGACATACGTCACCC
AGCGGCCGGTGTACCTCGGCCTGCCTGCAAATCTCGTTGACTTGAATGTCCCTGCAAAACTGTTGCAAAC
GCCAATCGATATGTCGTTGAAGCCCAATGACGCCGAATCCGAGAAAGAAGTCATTGATACCATCCTGGTG
CTGGCTAAGGATGCCAAGAATCCTGTCATCCTGGCTGATGCTTGCTGTAGCCGCCATGACGTTAAAGCTG
AAACAAAGAAACTGATCGACCTGACCCAGTTTCCCGCTTTTGTTACCCCTATGGGGAAGGGCTCGATCAG
TGAACAACATCCCGCTATGGCGGCGTCTATGTCGGTACTCTCAGCAAGCCCGAAGTCAAAGAAGCCGTT
GAGAGCGCAGATTTGATCTTGTCCGTTGGGGCTCTCTTGAGTGATTTCAACACCGGTTCCTTCAGTTATT
CTTATAAAACTAAAAACATCGTCGAGTTTCACAGTGACCACATGAAGATTCGTAATGCTACCTTTCCCGG
TGTCCAAATGAAATTCGTTTTGCAGAAGCTGTTGACTAATATCGCCGATGCTGCGAAGGGCTACAAACCC
GTCGCGGTTCCCGCGCGAACGCCCGCCAACGCAGCGGTCCCTGCTAGCACTCCGCTGAAGCAAGAATGGA
TGTGGAACCAACTCGGCAACTTCCTGCAGGAGGGCGATGTCGTGATTGCCGAGACTGGTACTTCGGCTTT
TGGTATTAACCAAACGACCTTTCCGAATAACACGTACGGCATCAGCCAAGTTCTGTGGGGCTCGATCGGC
TTCACCACGGGGGCCACGCTGGGCGCTGCATTTGCCGCAGAGGAAATTGACCCCAAGAAACGAGTGATCC
TCTTCATCGGCGATGGCTCCCTCCAACTGACGGTGCAAGAGATCAGTACCATGATCCGGTGGGGCCTGAA
GCCATACTTGTTCGTTCTGAACAATGATGGCTACACGATCGAAAAACTGATTCATGGCCCGAAAGCCCAA
TACAACGAAATTCAAGGTTGGGATCACCTGAGCCTGCTGCCCACGTTCGGCGCTAAAGATTATGAGACGC
ATCGCGTGGCCACAACGGGTGAATGGGATAAGCTGACGCAAGATAAGTCCTTTAACGACAATTCCAAGAT
TCGAATGATTGAAGTCATGCTGCCCGTCTTCGATGCTCCCCAAAACTTGGTCGAGCAGGCCAAGCTGACT
GCGGCGACGAACGCTAAGCAATAACTGTCGTTAACTGCTTTGTTGGTACTACCTGACTTCACCCTCTTTT
AAGATGAGCATCCCTGAAACACAGAAGGCTATTATCTTCTACGAAAGTAATGGTAAACTGGAACACAAGG
ACATTCCAGTGCCGAAACCCAAACCTAATGAGCTGCTGATTAATGTCAAATACAGCGGCGTGTGCCACAC
CGATTTGCACGCTTGGCACGGTGATTGGCCGCTCCCCACCAAGCTCCCCTTGGTGGGTGGACATGAGGGG
GCAGGGGTGGTTGTTGGAATGGGCGAGAACGTCAAGGGCTGGAAAATTGGTGATTATGCCGGTATTAAGT
GGCTGAACGGTTCGTGCATGGCGTGTGAATACTGCGAACTGGGAAACGAAAGCAACTGCCCTCATGCTGA
TCTCAGTGGTTACACCCACGACGGGAGTTTTCAGGAATATGCAACAGCTGATGCGGTTCAGGCTGCCCAC
ATTCCCCAGGGTACGGACCTGGCGGAAGTTGCCCCCATCTTGTGTGCTGGCATTACTGTCTACAAAGCCT
TGAAAAGTGCTAACCTGCGTGCGGGACACTGGGCAGCTATTTCTGGCGCAGCTGGTGGCCTCGGTTCCCT
GGCCGTTCAGTATGCCAAAGCTATGGGCTACCGTGTCTTGGGAATCGACGGTGGCCCCGGTAAAGAGGAA
TTGTTTACGAGCTTGGGCGGCGAAGTCTTTATTGACTTTACGAAAGAGAAGGATATTGTGAGCGCTGTTG
TGAAGGCTACCAATGGCGGTGCTCACGGTATCATCAATGTTAGCGTGTCCGAGGCCGCCATTGAAGCAAG
CACTCGGTATTGCCGGGCAAATGGAACCGTGGTGTTGGTCGGCCTCCCCGCAGGGGCGAAATGTAGCAGT
GATGTGTTTAACCATGTTGTGAAAAGTATTAGCATTGTTGGTTCGTACGTCGGCAATCGCGCAGATACCC
GCGAAGCCCTCGATTTCTTCGCTCGGGGCCTCGTCAAATCGCCCATCAAAGTCGTTGGTTTGAGCAGCCT
GCCGGAAATCTACGAAAGATGGAAAAAGGCCAGATTGCGGGTCGTTACGTGGTGGACACCAGTAAGTAG
GATCCATAAAACGAAAGGCTCAGTCGAAAGACTGGGCCTTTCGTTTTATCTGTTGTTTGTCGGTGAACGC
TCTCCTGAGTAGGACAAATCCGCCGGGAGCGGATTTGAACGTTGCGAAGCAACGGCCCGGAGGGTGGCGG
GCAGGACGCCCGCCATAAACTGCCAGGCATCAAATTAAGCAGAAGGCCATCCTGACGGATGGCCTTTTGA
GCTC   SEQ ID NO:1

FIG.3

```
ACTAGTTGTTGACAATTAATCATCCGGCTCGTATAATGTGTGGAATTGTGAGCGGATAACAATTTCACAC
AGGAAACAGACCATGGCTTATACTGTGGGGATTATTTGTTGGATAGGTTGCATGAATTAGGCATCGAGG
AAATCTTTGGTGTACCTGGAGATTACAATTTGCAATTTCTGGACCAGATCATATCGAGAGAGGATATGAA
ATGGATTGGTAACGCCAATGAATTAAATGCCAGCTATATGGCCGATGGCTATGCTCGTACCAAGAAAGCT
GCTGCTTTTCTGACAACTTTTGGTGTCGGTGAATTGTCTGCTATTAACGGACTGGCCGGTAGTTATGCTG
AAAATTTGCCAGTAGTTGAAATAGTCGGAAGCCCAACTTCTAAAGTGCAAAACGATGGCAAATTCGTGCA
TCATACTCTGGCAGATGGTGATTTTAAGCACTTCATGAAAATGCATGAACCCGTAACGGCTGCCAGAACT
CTTTTAACAGCCGAGAATGCGACATATGAAATTGATCGTGTACTTTCTCAGCTTTTAAAGGAGAGAAAAC
CTGTTTACATAAACTTACCTGTCGATGTTGCTGCTGCCAAAGCAGAGAAGCCAGCCCTGTCTCTTGAAAA
AGAAAGCTCCACCACCAACACTACCGAACAAGTGATATTATCTAAAATTGAGGAATCACTTAAAAACGCT
CAGAAACCAGTAGTCATAGCGGGTCATGAAGTCATAAGTTTCGGTCTTGAAAAGACTGTAACACAATTTG
TCAGCGAAACAAAATTGCCTATCACTACTTTGAACTTTGGCAAAAGTGCGGTCGACGAGTCGTTGCCATC
ATTTTTGGGTATCTACAATGGCAAACTATCAGAAATCTCATTGAAAAATTTCGTAGAAAGTGCGGATTTC
ATTCTGATGTTGGGCGTCAAGCTGACGGATTCTTCTACGGGGCTTTCACTCACCATTTGGATGAAAACA
AAATGATTTCATTGAACATCGATGAAGGGATCATCTTTAATAAGGTAGTGGAAGATTTCGATTTTAGAGC
CGTGGTTTCCTCCTTATCAGAGTTAAAAGGTATTGAGTACGAAGGGCAGTATATTGATAAGCAGTACGAG
GAATTTATTCCTTCTTCTGCTCCACTTTCTCAAGATCGTTTATGGCAAGCAGTCGAGTCCCTGACACAAA
GCAACGAGACTATAGTTGCAGAGCAAGGGACCTCATTCTTTGGTGCCTCTACAATTTTTCTGAAATCCAA
CAGCAGATTTATAGGACAACCCCTTTGGGGCTCTATTGGATATACTTTTCCCGCAGCCCTTGGTTCACAA
ATCGCAGATAAGGAGTCAAGACATCTGTTATTCATAGGTGATGGTAGTCTACAATTAACAGTTCAAGAAT
TAGGCCTATCAATAAGGGAGAAGTTAAACCCAATCTGTTTCATAATTAACAATGACGGCTACACTGTTGA
AAGGGAGATCCACGGACCAACACAATCATACAATGATATTCCCATGTGGAACTATAGCAAATTACCGGAG
ACTTTCGGCGCAACCGAGGATAGAGTAGTTTCGAAGATCGTTAGGACTGAGAATGAATTTGTTAGCGTTA
TGAAGGAAGCCCAGGCTGATGTCAATAGAATGTATTGGATTGAATTAGTTTTGGAAAAGGAAGATGCACC
TAAATTACTAAAAAGATGGGGAAACTATTTGCTGAGCAAAACAAATAACTGTCGTTAACTGCTTTGTTG
GTACTACCTGACTTCACCCTCTTTTAAGATGAGCATCCCTGAAACACAGAAGGCTATTATCTTCTACGAA
AGTAATGGTAAACTGGAACACAAGGACATTCCAGTGCCGAAACCCAAACCTAATGAGCTGCTGATTAATG
TCAAATACAGCGGCGTGTGCCACACCGATTTGCACGCTTGGCACGGTGATTGGCCGCTCCCCACCAAGCT
CCCCTTGGTGGGTGGACATGAGGGGGCAGGGGTGGTTGTTGGAATGGGCGAGAACGTCAAGGGCTGGAAA
ATTGGTGATTATGCCGGTATTAAGTGGCTGAACGGTTCGTGCATGGCGTGTGAATACTGCGAACTGGGAA
ACGAAAGCAACTGCCCTCATGCTGATCTCAGTGGTTACACCCACGACGGGAGTTTTCAGGAATATGCAAC
AGCTGATGCGGTTCAGGCTGCCCACATTCCCCAGGGTACGGACCTGGCGGAAGTTGCCCCCATCTTGTGT
GCTGGCATTACTGTCTACAAAGCCTTGAAAAGTGCTAACCTGCGTGCGGGACACTGGGCAGCTATTTCTG
GCGCAGCTGGTGGCCTCGGTTCCCTGGCCGTTCAGTATGCCAAAGCTATGGGCTACCGTGTCTTGGGAAT
CGACGGTGGCCCCGGTAAAGAGGAATTGTTTACGAGCTTGGGCGGCGAAGTCTTTATTGACTTTACGAAA
GAGAAGGATATTGTGAGCGCTGTTGTGAAGGCTACCAATGGCGGTGCTCACGGTATCATCAATGTTAGCG
TGTCCGAGGCCGCCATTGAAGCAAGCACTCGGTATTGCCGGGCAAATGGAACCGTGGTGTTGGTCGGCCT
CCCCGCAGGGGCGAAATGTAGCAGTGATGTGTTTAACCATGTTGTGAAAAGTATTAGCATTGTTGGTTCG
TACGTCGGCAATCGCGCAGATACCCGCGAAGCCCTCGATTTCTTCGCTCGGGCCTCGTCAAATCGCCCA
TCAAAGTCGTTGGTTTGAGCAGCCTGCCGGAAATCTACGAAAGATGGAAAAAGGCCAGATTGCGGGTCG
TTACGTGGTGGACACCAGTAAGTAGGATCCATAAAACGAAAGGCTCAGTCGAAAGACTGGGCCTTTCGTT
TTATCTGTTGTTTGTCGGTGAACGCTCTCCTGAGTAGGACAAATCCGCCGGGAGCGGATTTGAACGTTGC
GAAGCAACGGCCCGGAGGGTGGCGGGCAGGACGCCCGCCATAAACTGCCAGGCATCAAATTAAGCAGAAG
GCCATCCTGACGGATGGCCTTTTGAGCTC    SEQ ID NO:2
```

FIG.4

```
ACTAGTTGTTGACAATTAATCATCCGGCTCGTATAATGTGTGGAATTGTGAGCGGATAACAATTTCACAC
AGGAAACAGACCATGGCTGAAATCACGCTGGGAAAATATCTGTTTGAACGGTTGAAGCAAGTCAATGTGA
ACACCGTGTTTGGCCTGCCTGGGGATTTCAACTTGAGTCTGTTGGACAAAATCTATGAAGTGGAAGGCAT
GCGATGGGCCGGTAACGCGAATGAGTTGAATGCGCGTTATGCTGCTGATGGTTACGCACGAATCAAGGGA
ATGAGCTGTATTATTACTACATTCGGTGTCGGCGAGCTGAGCGCATTGAATGGCATTGCTGGTTCCTACG
CAGAACATGTGGGGGTTCTCCATGTGGTGGGGGTGCCAAGCATCTCCAGCCAGGCGAAGCAATTGCTCCT
CCACCACACCTTGGGTAACGGGGATTTTACCGTCTTCCACCGGATGTCGGCAAATATCTCTGAGACAACG
GCCATGATCACTGATATTTGCACCGCGCCAGCCGAAATCGATCGGTGTATCCGTACGACATACGTCACCC
AGCGGCCGGTGTACCTCGGCCTGCCTGCAAATCTCGTTGACTTGAATGTCCCTGCAAAACTGTTGCAAAC
GCCAATCGATATGTCGTTGAAGCCCAATGACGCCGAATCCGAGAAAGAAGTCATTGATACCATCCTGGTG
CTGGCTAAGGATGCCAAGAATCCTGTCATCCTGGCTGATGCTTGCTGTAGCCGCCATGACGTTAAAGCTG
AAACAAAGAAACTGATCGACCTGACCCAGTTTCCCGCTTTTGTTACCCCTATGGGGAAGGGCTCGATCAG
TGAACAACATCCCCGCTATGGCGGCGTCTATGTCGGTACTCTCAGCAAGCCCGAAGTCAAAGAAGCCGTT
GAGAGCGCAGATTTGATCTTGTCCGTTGGGCTCTCTTGAGTGATTTCAACACCGGTTCCTTCAGTTATT
CTTATAAAACTAAAAACATCGTCGAGTTTCACAGTGACCACATGAAGATTCGTAATGCTACCTTTCCCGG
TGTCCAAATGAAATTCGTTTTGCAGAAGCTGTTGACTAATATCGCCGATGCTGCGAAGGGCTACAAACCC
GTCGCGGTTCCCGCGCGAACGCCCGCCAACGCAGCGGTCCCTGCTAGCACTCCGCTGAAGCAAGAATGGA
TGTGGAACCAACTCGGCAACTTCCTGCAGGAGGGCGATGTCGTGATTGCCGAGACTGGTACTTCGGCTTT
TGGTATTAACCAAACGACCTTTCCGAATAACACGTACGGCATCAGCCAAGTTCTGTGGGGCTCGATCGGC
TTCACCACGGGGGCCACGCTGGGCGCTGCATTTGCCGCAGAGGAAATTGACCCCAAGAAACGAGTGATCC
TCTTCATCGGCGATGGCTCCCTCCAACTGACGGTGCAAGAGATCAGTACCATGATCCGGTGGGGCCTGAA
GCCATACTTGTTCGTTCTGAACAATGATGGCTACACGATCGAAAAACTGATTCATGCCCGAAAGCCCAA
TACAACGAAATTCAAGGTTGGGATCACCTGAGCCTGCTGCCCACGTTCGGCGCTAAAGATTATGAGACGC
ATCGCGTGGCCACAACGGGTGAATGGGATAAGCTGACGCAAGATAAGTCCTTTAACGACAATTCCAAGAT
TCGAATGATTGAAGTCATGCTGCCCGTCTTCGATGCTCCCCAAAACTTGGTCGAGCAGGCCAAGCTGACT
GCGGCGACGAACGCTAAGCAATAACTGTCGTTAACTGCTTTGTTGGTACTACCTGACTTCACCCTCTTTT
AAGATGTCTTATCCTGAGAAATTTGAAGGTATCGCTATTCAATCACACGAAGATTGGAAAAACCCAAAGA
AGACAAAGTATGACCCAAAACCATTTTACGATCATGACATTGACATTAAGATCGAAGCATGTGGTGTCTG
CGGTAGTGATATTCATTGTGCAGCTGGTCATTGGGGCAATATGAAGATGCCGCTAGTCGTTGGTCATGAA
ATCGTTGGTAAAGTTGTCAAGCTAGGGCCCAAGTCAAACAGTGGGTTGAAAGTCGGTCAACGTGTTGGTG
TAGGTGCTCAAGTCTTTTCATGCTTGGAATGTGACCGTTGTAAGAATGATAATGAACCATACTGCACCAA
GTTTGTTACCACATACAGTCAGCCTTATGAAGACGGCTATGTGTCGCAGGGTGGCTATGCAAACTACGTC
AGAGTTCATGAACATTTTGTGGTGCCTATCCAGAGAATATTCCATCACATTTGGCTGCTCCACTATTAT
GTGGTGGTTTGACTGTGTACTCTCCATTGGTTCGTAACGGTTGCGGTCCAGGTAAAAAGTTGGTATAGT
TGGTCTTGGTGGTATCGGCAGTATGGGTACATTGATTTCCAAAGCCATGGGGCAGAGACGTATGTTATT
TCTCGTTCTTCGAGAAAAGAGAAGATGCAATGAAGATGGGCGCCGATCACTACATTGCTACATTAGAAG
AAGGTGATTGGGGTGAAAAGTACTTTGACACCTTCGACCTGATTGTAGTCTGTGCTTCCTCCCTTACCGA
CATTGACTTCAACATTATGCCAAAGGCTATGAAGGTTGGTGGTAGAATTGTCTCAATCTCTATACCAGAA
CAACACGAAATGTTATCGCTAAAGCCATATGGCTTAAAGGCTGTCTCCATTTCTTACAGTGCTTTAGGTT
CCATCAAAGAATTGAACCAACTCTTGAAATTAGTCTCTGAAAAAGATATCAAAATTTGGGTGGAAACATT
ACCTGTTGGTGAAGCCGGCGTCCATGAAGCCTTCGAAAGGATGGAAAGGGTGACGTTAGATATAGATTT
ACCTTAGTCGGCTACGACAAAGAATTTTCAGACTAGGATCCATAAAACGAAAGGCTCAGTCGAAAGACTG
GGCCTTTCGTTTTATCTGTTGTTTGTCGGTAACGCTCTCCTGAGTAGGACAAATCGCCGGGAGCGGAT
TTGAACGTTGCGAAGCAACGGCCCGGAGGGTGGCGGGCAGGACGCCCGCCATAAACTGCCAGGCATCAAA
TTAAGCAGAAGGCCATCCTGACGGATGGCCTTTTGAGCTC    SEQ ID NO:3
```

FIG.5

```
ACTAGTTGTTGACAATTAATCATCCGGCTCGTATAATGTGTGGAATTGTGAGCGGATAACAATTTCACAC
AGGAAACAGACCATGGCTTATACTGTGGGGATTATTTGTTGGATAGGTTGCATGAATTAGGCATCGAGG
AAATCTTTGGTGTACCTGGAGATTACAATTTGCAATTTCTGGACCAGATCATATCGAGAGAGGATATGAA
ATGGATTGGTAACGCCAATGAATTAAATGCCAGCTATATGGCCGATGGCTATGCTCGTACCAAGAAAGCT
GCTGCTTTTCTGACAACTTTTGGTGTCGGTGAATTGTCTGCTATTAACGGACTGGCCGGTAGTTATGCTG
AAAATTTGCCAGTAGTTGAAATAGTCGGAAGCCCAACTTCTAAAGTGCAAAACGATGGCAAATTCGTGCA
TCATACTCTGGCAGATGGTGATTTTAAGCACTTCATGAAAATGCATGAACCCGTAACGGCTGCCAGAACT
CTTTTAACAGCCGAGAATGCGACATATGAAATTGATCGTGTACTTTCTCAGCTTTTAAAGGAGAGAAAAC
CTGTTTACATAAACTTACCTGTCGATGTTGCTGCTGCCAAAGCAGAGAAGCCAGCCCTGTCTCTTGAAAA
AGAAAGCTCCACCACCAACACTACCGAACAAGTGATATTATCTAAAATTGAGGAATCACTTAAAAACGCT
CAGAAACCAGTAGTCATAGCGGGTCATGAAGTCATAAGTTTCGGTCTTGAAAAGACTGTAACACAATTTG
TCAGCGAAACAAAATTGCCTATCACTACTTTGAACTTTGGCAAAAGTGCGGTCGACGAGTCGTTGCCATC
ATTTTTGGGTATCTACAATGGCAAACTATCAGAAATCTCATTGAAAAATTTCGTAGAAAGTGCGGATTTC
ATTCTGATGTTGGGCGTCAAGCTGACGGATTCTTCTACGGGGCTTTCACTCACCATTTGGATGAAAACA
AAATGATTTCATTGAACATCGATGAAGGGATCATCTTTAATAAGGTAGTGGAAGATTTCGATTTTAGAGC
CGTGGTTTCCTCCTTATCAGAGTTAAAAGGTATTGAGTACGAAGGGCAGTATATTGATAAGCAGTACGAG
GAATTTATTCCTTCTTCTGCTCCACTTTCTCAAGATCGTTTATGGCAAGCAGTCGAGTCCCTGACACAAA
GCAACGAGACTATAGTTGCAGAGCAAGGGACCTCATTCTTTGGTGCCTCTACAATTTTTCTGAAATCCAA
CAGCAGATTTATAGGACAACCCCTTTGGGGCTCTATTGGATATACTTTTCCCGCAGCCCTTGGTTCACAA
ATCGCAGATAAGGAGTCAAGACATCTGTTATTCATAGGTGATGGTAGTCTACAATTAACAGTTCAAGAAT
TAGGCCTATCAATAAGGGAGAAGTTAAACCCAATCTGTTTCATAATTAACAATGACGGCTACACTGTTGA
AAGGGAGATCCACGGACCAACACAATCATACAATGATATTCCCATGTGGAACTATAGCAAATTACCGGAG
ACTTTCGGCGCAACCGAGGATAGAGTAGTTTCGAAGATCGTTAGGACTGAGAATGAATTTGTTAGCGTTA
TGAAGGAAGCCCAGGCTGATGTCAATAGAATGTATTGGATTGAATTAGTTTTGGAAAAGGAAGATGCACC
TAAATTACTAAAAAAGATGGGGAAACTATTTGCTGAGCAAAACAAATAACTGTCGTTAACTGCTTTGTTG
GTACTACCTGACTTCACCCTCTTTTAAGATGTCTTATCCTGAGAAATTTGAAGGTATCGCTATTCAATCA
CACGAAGATTGGAAAAACCCAAAGAAGACAAAGTATGACCCAAAACCATTTTACGATCATGACATTGACA
TTAAGATCGAAGCATGTGGTGTCTGCGGTAGTGATATTCATTGTGCAGCTGGTCATTGGGCAATATGAA
GATGCCGCTAGTCGTTGGTCATGAAATCGTTGGTAAAGTTGTCAAGCTAGGGCCCAAGTCAAACAGTGGG
TTGAAAGTCGGTCAACGTGTTGGTGTAGGTGCTCAAGTCTTTTCATGCTTGGAATGTGACCGTTGTAAGA
ATGATAATGAACCATACTGCACCAAGTTTGTTACCACATACAGTCAGCCTTATGAAGACGGCTATGTGTC
GCAGGGTGGCTATGCAAACTACGTCAGAGTTCATGAACATTTTGTGGTGCCTATCCCAGAGAATATTCCA
TCACATTTGGCTGCTCCACTATTATGTGGTGGTTTGACTGTGTACTCTCCATTGGTTCGTAACGGTTGCG
GTCCAGGTAAAAAGTTGGTATAGTTGGTCTTGGTGGTATCGGCAGTATGGGTACATTGATTTCCAAAGC
CATGGGGCAGAGACGTATGTTATTTCTCGTTCTTCGAGAAAAGAGAAGATGCAATGAAGATGGGCGCC
GATCACTACATTGCTACATTAGAAGAAGGTGATTGGGGTGAAAAGTACTTTGACACCTTCGACCTGATTG
TAGTCTGTGCTTCCTCCCTTACCGACATTGACTTCAACATTATGCCAAAGGCTATGAAGGTTGGTGGTAG
AATTGTCTCAATCTCTATACCAGAACAACACGAAATGTTATCGCTAAAGCCATATGGCTTAAAGGCTGTC
TCCATTTCTTACAGTGCTTTAGGTTCCATCAAAGAATTGAACCAACTCTTGAAATTAGTCTCTGAAAAAG
ATATCAAAATTTGGGTGGAAACATTACCTGTTGGTGAAGCCGGCGTCCATGAAGCCTTCGAAAGGATGGA
AAAGGGTGACGTTAGATATAGATTTACCTTAGTCGGCTACGACAAAGAATTTTCAGACTAGGATCCATAA
AACGAAAGGCTCAGTCGAAAGACTGGGCCTTTCGTTTATCTGTTGTTTGTCGGTGAACGCTCTCCTGAG
TAGGACAAATCCGCCGGGAGCGGATTTGAACGTTGCGAAGCAACGGCCCGGAGGGTGGCGGGCAGGACGC
CCGCCATAAACTGCCAGGCATCAAATTAAGCAGAAGGCCATCCTGACGGATGGCCTTTTGAGCTC
```
SEQ ID NO:4

ACTAGTCCTGAGGTGTTGACAATTAATCATCCGGCTCGTATAATGTGTGGAATTGTGAGCGGATAACAAT
TTCACACAGGAAACAGACCATGTTAGGGCAAATGAACACCGCAGACCTATTGGTTCAATGTCTGGAAAAT
GAGGACGTTGAATACATTTTTGGCGTACCCGGAGAGGAAAACCTCCACATCCTCGAAGCGCTGAAAAACT
CGCCCATCCGCTTTATTACCACCCGCCACGAACAGGGAGCAGCCTTTATGGCCGACGTTTACGGCCGTTT
AACGGGCAAAGCGGGGGTTTGTCTTTCCACCCTGGGGCCTGGAGCCACCAACCTGATGACCGGGGTAGCG
GATGCTAACTTGGACGGAGCGCCCTGGTGGCCATCACTGGACAGGTGGGCACAGATCGGATGCACATCG
AATCCCACCAATACCTGGACTTGGTGGCCATGTTCGACCCGGTGACTAAATGGACCAGGCAAATTGTCCG
CCCCAGCATTACCCCGGAAGTGGTTCGTAAAGCGTTCAAATTGGCTCAGAGCGAAAAACCAGGGGCCACC
CACATTGATTTACCAGAAAATATTGCCGCTATGCCGGTGGATGGGAAACCCCTACGGCGGGACAGTCGGG
AAAAGGTTTATGCAGCTTTTCGTACTTTGGGCACAGCGGCCAACGCCATTTCCAAGGCCAAAAACCCCAT
TATTCTGGCCGGCAATGGCACCATCCGAGCCGAAGCCAGCGAAGCCCTGACGGAATTTGCCACCAGTTTG
AATATTCCCGTGGCCAACACCTTCATGGGTAAAGGCACCATGCCCTACACCCATCCCCTTTCCCTTTGGA
CAGTGGGCTTACAACAACGGGATCACATTACCTGTGCCTTTGAAAAAAGCGATTTGGTCATTGCGGTGGG
CTATGACTTAATTGAATATTCTCCGAAAAAATGGAATCCCACTGGAGATTTGCCCATCATTCACATTGGC
GCTACTCCGGCGGAAATTGATAGCAGTTATATTCCCCAGGTGGAGGTGGTGGGGGACATTACCGATTCCC
TGATGGATTTGCTCAAACGGTGCGATCGCCAAGGTAAACCCACTCCCTACGGGGCTTCTCTCCGGGCGGA
AATTCGGGCCGAGTATGAATGTTATGCCAATGACACAGGTTTTCCCGTTAAGCCACAAAAAATTATTTAT
GACCTGCGCCAAGTGATGGGCCCCGATGATGTGGTGATTTCCGATGTGGGGGCCCATAAAATGTGGATGG
CCCGCCATTACCACTGTGACAGCCCCAACACCTGTTTAATTTCCAATGGTTTTGCGGCCATGGGCATTGC
CATTCCAGGGGCGATCGCCGCTAAGCTGGTTTATCCTGAGCGCAACATTGTTGCAGTGACGGGGGACGGC
GGTTTTATGATGAACTGTCAGGAGTTGGAAACGGCCATGCGGGTGGGCACTCCCTTTGTCACGTTGATTT
TTAACGACAACGGTTACGGCCTAATTGAGTGGAAACAGATCAACCAATTTGGCGAATCCAGCTTTATTAA
ATTTGGCAATCCAGACTTTGTTAAGTTTGCTGAAAGTATGGGTCTCAAAGGTTATCGGGTGGAAGCGGCG
GCGGATTTAATTCCTATCCTCAAAGAAGCTTTAGCTCAACCTGTGCCCACAGTGATTGATTGTCCTGTGG
ATTATCGGGAGAATATTCGTTTCTCGCAAAAAGCAGGGGAATTGGCCTGTGAAATTTGGGAATAAAGATC
TGATCCGCTGTTGACCCAACAGCATGAGTCGTTATCCAAGGGGAGCTTCGGCTCCCTTTTTTCATGCGCG
GATGCGGTGAGAGCTC  SEQ ID NO:7

FIG.7

MTPVQETIRLPGTSSPTVPENVTLGEYLFLRISQANPKLRSIFGIPGDFNVDLLEHLYSPVVAGRDIKFI
GLCNELNGAYTADGYSRAIGGLSTFISTFGVGELSAINGIAGSFAEFSPVLHIVGTTSLPQRDHAINGSD
VRNHHHLIQNKNPLCQPNHDVYKKMIEPISVIQESLDSDLQRNMEKIDRVLVKILQESRPGYLFIPCDIT
NLIVPSYRLYETPLPLEIQLTTSGVEVLEDVVDAILFRLYKSKNPSLLSDCLTTRFNLQDKLNTLVAKLP
SNFVKLFSTNMARNIDESLSNFVGLYFGIGSSSKEVSRQLERNTDFLINLGYFNAETTTAGYSNDFSNIE
EYIEINPDYIKVNEHIINIKNPESGKRLFSMGQLLDALLFKLDLNKIENINNNNISYKFFPPTLYEQDNN
TDYIPQTKLVDYLNENLQPGDLLVMDTMSFCFALPDIMLPQGVQLLTQNYYGSIGYALPSTFGATMAVND
LGSDRRIILIEGDGAAQMTIQELSSFLKYKEFLPNMPKIFLINNDGYTVERMIKGPTRSYNDINGEWSWT
QLLGVFGDKEQKYHSTALLRNVNEFNKYFEFQRQTDNSKLEFIELIAGKYDCPLRFSEMFCKK
(SEQ ID NO:8)

FIG. 8

SEQUENCE LISTING

<160> NUMBER OF SEQ ID NOS: 8

<210> SEQ ID NO 1
<211> LENGTH: 3084
<212> TYPE: DNA
<213> ORGANISM: Artificial sequence
<220> FEATURE:
<223> OTHER INFORMATION: PDC1- ADH2 expression operon

<400> SEQUENCE: 1

```
actagttgtt gacaattaat catccggctc gtataatgtg tggaattgtg agcggataac      60
aatttcacac aggaaacaga ccatggctga aatcacgctg ggaaaatatc tgtttgaacg     120
gttgaagcaa gtcaatgtga acaccgtgtt tggcctgcct ggggatttca acttgagtct     180
```

```
gttggacaaa atctatgaag tggaaggcat gcgatgggcc ggtaacgcga atgagttgaa    240
tgcgcgttat gctgctgatg gttacgcacg aatcaaggga atgagctgta ttattactac    300
attcggtgtc ggcgagctga gcgcattgaa tggcattgct ggttcctacg cagaacatgt    360
gggggttctc catgtggtgg gggtgccaag catctccagc caggcgaagc aattgctcct    420
ccaccacacc ttgggtaacg gggattttac cgtcttccac cggatgtcgg caaatatctc    480
tgagacaacg gccatgatca ctgatatttg caccgcgcca gccgaaatcg atcggtgtat    540
ccgtacgaca tacgtcaccc agcggccggt gtacctcggc ctgcctgcaa atctcgttga    600
cttgaatgtc cctgcaaaac tgttgcaaac gccaatcgat atgtcgttga agcccaatga    660
cgccgaatcc gagaaagaag tcattgatac catcctggtg ctggctaagg atgccaagaa    720
tcctgtcatc ctggctgatg cttgctgtag ccgccatgac gttaaagctg aaacaaagaa    780
actgatcgac ctgacccagt ttcccgcttt tgttacccct atggggaagg gctcgatcag    840
tgaacaacat ccccgctatg gcggcgtcta tgtcggtact ctcagcaagc ccgaagtcaa    900
agaagccgtt gagagcgcag atttgatctt gtccgttggg gctctcttga gtgatttcaa    960
caccggttcc ttcagttatt cttataaaac taaaaacatc gtcgagtttc acagtgacca   1020
catgaagatt cgtaatgcta ccttttcccgg tgtccaaatg aaattcgttt tgcagaagct   1080
gttgactaat atcgccgatg ctgcgaaggg ctacaaaccc gtcgcggttc ccgcgcgaac   1140
gcccgccaac gcagcggtcc ctgctagcac tccgctgaag caagaatgga tgtggaacca   1200
actcggcaac ttcctgcagg agggcgatgt cgtgattgcc gagactggta cttcggcttt   1260
tggtattaac caaacgacct ttccgaataa cacgtacggc atcagccaag ttctgtgggg   1320
ctcgatcggc ttcaccacgg gggccacgct gggcgctgca tttgccgcag aggaaattga   1380
ccccaagaaa cgagtgatcc tcttcatcgg cgatggctcc ctccaactga cggtgcaaga   1440
gatcagtacc atgatccggt ggggcctgaa gccatacttg ttcgttctga caatgatgg   1500 ctacacgatc gaaaaactga ttcatggccc gaaagcccaa taacgaaa ttcaaggttg   1560 ggatcacctg agcctgctgc ccacgttcgg cgctaaagat tatgagacgc atcgcgtggc   1620
cacaacgggt gaatgggata agctgacgca agataagtcc tttaacgaca attccaagat   1680
tcgaatgatt gaagtcatgc tgcccgtctt cgatgctccc caaaacttgg tcgagcaggc   1740
caagctgact gcggcgacga acgctaagca ataactgtcg ttaactgctt tgttggtact   1800
acctgacttc accctctttt aagatgagca tccctgaaac acagaaggct attatcttct   1860
acgaaagtaa tggtaaactg gaacacaagg acattccagt gccgaaaccc aaacctaatg   1920
agctgctgat taatgtcaaa tacagcggcg tgtgccacac cgatttgcac gcttggcacg   1980
gtgattggcc gctccccacc aagctcccct tggtgggtgg acatgagggg gcaggggtgg   2040
ttgttggaat gggcgagaac gtcaagggct ggaaaattgg tgattatgcc ggtattaagt   2100
ggctgaacgg ttcgtgcatg gcgtgtgaat actgcgaact gggaaacgaa agcaactgcc   2160
ctcatgctga tctcagtggt tacacccacg acgggagttt tcaggaatat gcaacagctg   2220
atgcggttca ggctgcccac attccccagg gtacggacct ggcggaagtt gccccccatct   2280 tgtgtgctgg cattactgtc tacaaagcct tgaaaagtgc taacctgcgt gcgggacact   2340
gggcagctat ttctggcgca gctggtgcc tcggttccct ggccgttcag tatgccaaag   2400
ctatgggcta ccgtgtcttg ggaatcgacg gtggccccgg taagaggaa ttgtttacga   2460 gcttgggcgg cgaagtcttt attgacttta cgaaagagaa ggatattgtg agcgctgttg   2520
tgaaggctac caatggcggt gctcacggta tcatcaatgt tagcgtgtcc gaggccgcca   2580
```

```
ttgaagcaag cactcggtat tgccgggcaa atggaaccgt ggtgttggtc ggcctccccg    2640
caggggcgaa atgtagcagt gatgtgttta accatgttgt gaaaagtatt agcattgttg    2700
gttcgtacgt cggcaatcgc gcagataccc gcgaagccct cgatttcttc gctcggggcc    2760
tcgtcaaatc gcccatcaaa gtcgttggtt tgagcagcct gccggaaatc tacgaaaaga    2820
tggaaaaagg ccagattgcg ggtcgttacg tggtggacac cagtaagtag gatccataaa    2880
acgaaaggct cagtcgaaag actgggcctt tcgttttatc tgttgtttgt cggtgaacgc    2940
tctcctgagt aggacaaatc cgccgggagc ggatttgaac gttgcgaagc aacggcccgg    3000
agggtggcgg gcaggacgcc cgccataaac tgccaggcat caaattaagc agaaggccat    3060
cctgacggat ggcctttga gctc                                           3084
```

<210> SEQ ID NO 2
<211> LENGTH: 3039
<212> TYPE: DNA
<213> ORGANISM: Artificial sequence
<220> FEATURE:
<223> OTHER INFORMATION: KDCa- ADH2 expression operon

<400> SEQUENCE: 2

```
actagttgtt gacaattaat catccggctc gtataatgtg tggaattgtg agcggataac      60
aatttcacac aggaaacaga ccatggctta tactgtgggg gattatttgt tggataggtt     120
gcatgaatta ggcatcgagg aaatctttgg tgtacctgga gattacaatt gcaatttct     180 ggaccagatc atatcgagag aggatatgaa atggattggt aacgccaatg aattaaatgc     240
cagctatatg gccgatggct atgctcgtac caagaaagct gctgcttttc tgacaacttt     300
tggtgtcggt gaattgtctg ctattaacgg actggccggt agttatgctg aaaatttgcc     360
agtagttgaa atagtcggaa gcccaacttc taaagtgcaa aacgatggca aattcgtgca     420
tcatactctg gcagatggtg attttaagca cttcatgaaa atgcatgaac ccgtaacggc     480
tgccagaact cttttaacag ccgagaatgc gacatatgaa attgatcgtg tactttctca     540
gcttttaaag gagagaaaac ctgtttacat aaacttacct gtcgatgttg ctgctgccaa     600
agcagagaag ccagccctgt ctcttgaaaa agaaagctcc accaccaaca ctaccgaaca     660
agtgatatta tctaaaattg aggaatcact taaaaacgct cagaaaccag tagtcatagc     720
gggtcatgaa gtcataagtt tcggtcttga aaagactgta acacaatttg tcagcgaaac     780
aaaattgcct atcactactt tgaactttgg caaaagtgcg gtcgacgagt cgttgccatc     840
atttttgggt atctacaatg gcaaactatc agaaatctca ttgaaaaatt tcgtagaaag     900
tgcggatttc attctgatgt gggcgtcaa gctgacggat tcttctacgg gggctttcac     960
tcaccatttg gatgaaaca aaatgattc attgaacatc gatgaaggga tcatctttaa    1020
taaggtagtg gaagatttcg attttagagc cgtggtttcc tccttatcag agttaaaagg    1080
tattgagtac gaagggcagt atattgataa gcagtacgag gaatttattc cttcttctgc    1140
tccactttct caagatcgtt tatggcaagc agtcgagtcc ctgacacaaa gcaacgagac    1200
tatagttgca gagcaaggga cctcattctt tggtgcctct acaattttc tgaaatccaa    1260 cagcagattt ataggacaac ccctttgggg ctctattgga tatacttttc ccgcagccct    1320
tggttcacaa atcgcagata aggagtcaag acatctgtta ttcataggtg atggtagtct    1380
acaattaaca gttcaagaat taggcctatc aataagggag aagttaaacc caatctgttt    1440
cataattaac aatgacggct acactgttga aagggagatc cacggaccaa cacaatcata    1500
```

```
caatgatatt cccatgtgga actatagcaa attaccggag actttcggcg caaccgagga      1560
tagagtagtt tcgaagatcg ttaggactga gaatgaattt gttagcgtta tgaaggaagc      1620
ccaggctgat gtcaatagaa tgtattggat tgaattagtt ttggaaaagg aagatgcacc      1680
taaattacta aaaagatgg ggaaactatt tgctgagcaa acaaataac tgtcgttaac       1740
tgctttgttg gtactacctg acttcaccct cttttaagat gagcatccct gaaacacaga      1800
aggctattat cttctacgaa agtaatggta aactggaaca caaggacatt ccagtgccga      1860
aacccaaacc taatgagctg ctgattaatg tcaaatacag cggcgtgtgc cacaccgatt      1920
tgcacgcttg gcacggtgat tggccgctcc ccaccaagct cccccttggtg ggtggacatg      1980
agggggcagg ggtggttgtt ggaatgggcg agaacgtcaa gggctggaaa attggtgatt      2040
atgccggtat taagtggctg aacggttcgt gcatggcgtg tgaatactgc gaactgggaa      2100
acgaaagcaa ctgccctcat gctgatctca gtggttacac ccacgacggg agttttcagg      2160
aatatgcaac agctgatgcg gttcaggctg cccacattcc ccagggtacg gacctggcgg      2220
aagttgcccc catcttgtgt gctggcatta ctgtctacaa agccttgaaa agtgctaacc      2280
tgcgtgcggg acactgggca gctatttctg gcgcagctgg tggcctcggt tccctggccg      2340
ttcagtatgc caaagctatg ggctaccgtg tcttgggaat cgacggtggc cccggtaaag      2400
aggaattgtt tacgagcttg ggcggcgaag tctttattga ctttacgaaa gagaaggata      2460
ttgtgagcgc tgttgtgaag gctaccaatg gcggtgctca cggtatcatc aatgttagcg      2520
tgtccgaggc cgccattgaa gcaagcactc ggtattgccg ggcaaatgga accgtggtgt      2580
tggtcggcct ccccgcaggg gcgaaatgta gcagtgatgt gtttaaccat gttgtgaaaa      2640
gtattagcat tgttggttcg tacgtcggca atcgcgcaga tacccgcgaa gccctcgatt      2700
tcttcgctcg gggcctcgtc aaatcgccca tcaaagtcgt tggtttgagc agcctgccgg      2760
aaatctacga aaagatggaa aaaggccaga ttgcgggtcg ttacgtggtg gacaccagta      2820
agtaggatcc ataaaacgaa aggctcagtc gaaagactgg gcctttcgtt ttatctgttg      2880
tttgtcggtg aacgctctcc tgagtaggac aaatccgccg ggagcggatt tgaacgttgc      2940
gaagcaacgg cccggagggt ggcgggcagg acgcccgcca taaactgcca ggcatcaaat      3000
taagcagaag gccatcctga cggatggcct tttgagctc                             3039
```

<210> SEQ ID NO 3
<211> LENGTH: 3120
<212> TYPE: DNA
<213> ORGANISM: Artificial sequence
<220> FEATURE:
<223> OTHER INFORMATION: PDC1- ADH6 expression operon

<400> SEQUENCE: 3

```
actagttgtt gacaattaat catccggctc gtataatgtg tggaattgtg agcggataac        60
aatttcacac aggaaacaga ccatggctga atcacgctg ggaaaatatc tgtttgaacg       120
gttgaagcaa gtcaatgtga acaccgtgtt tggcctgcct ggggatttca acttgagtct       180
gttggacaaa atctatgaag tggaaggcat gcgatgggcc ggtaacgcga atgagttgaa       240
tgcgcgttat gctgctgatg gttacgcacg aatcaaggga atgagctgta ttattactac       300
attcggtgtc ggcgagctga gcgcattgaa tggcattgct ggttcctacg cagaacatgt       360
gggggttctc catgtggtgg gggtgccaag catctccagc caggcgaagc aattgctcct       420
ccaccacacc ttgggtaacg gggattttac cgtcttccac cggatgtcgg caaatatctc       480
tgagacaacg gccatgatca ctgatatttg caccgcgcca gccgaaatcg atcggtgtat       540
```

```
ccgtacgaca tacgtcaccc agcggccggt gtacctcggc ctgcctgcaa atctcgttga    600
cttgaatgtc cctgcaaaac tgttgcaaac gccaatcgat atgtcgttga agcccaatga    660
cgccgaatcc gagaaagaag tcattgatac catcctggtg ctggctaagg atgccaagaa    720
tcctgtcatc ctggctgatg cttgctgtag ccgccatgac gttaaagctg aaacaaagaa    780
actgatcgac ctgacccagt tcccgctttt tgttacccct atggggaagg ctcgatcag    840 tgaacaacat ccccgctatg gcggcgtcta tgtcggtact ctcagcaagc ccgaagtcaa    900
agaagccgtt gagagcgcag atttgatctt gtccgttggg gctctcttga gtgatttcaa    960
caccggttcc ttcagttatt cttataaaac taaaaacatc gtcgagtttc acagtgacca   1020
catgaagatt cgtaatgcta cctttcccgg tgtccaaatg aaattcgttt tgcagaagct   1080
gttgactaat atcgccgatg ctgcgaaggg ctacaaaccc gtcgcggttc ccgcgcgaac   1140
gcccgccaac gcagcggtcc ctgctagcac tccgctgaag caagaatgga tgtggaacca   1200
actcggcaac ttcctgcagg agggcgatgt cgtgattgcc gagactggta cttcggcttt   1260
tggtattaac caaacgacct ttccgaataa cacgtacggc atcagccaag ttctgtgggg   1320
ctcgatcggc ttcaccacgg gggccacgct gggcgctgca tttgccgcag aggaaattga   1380
ccccaagaaa cgagtgatcc tcttcatcgg cgatggctcc ctccaactga cggtgcaaga   1440
gatcagtacc atgatccggt ggggcctgaa gccatacttg ttcgttctga caatgatgg    1500 ctacacgatc gaaaaactga ttcatggccc gaaagcccaa tacaacgaaa ttcaaggttg   1560
ggatcacctg agcctgctgc ccacgttcgg cgctaaagat tatgagacgc atcgcgtggc   1620
cacaacgggt gaatgggata agctgacgca agataagtcc tttaacgaca attccaagat   1680
tcgaatgatt gaagtcatgc tgcccgtctt cgatgctccc caaaacttgg tcgagcaggc   1740
caagctgact gcggcgacga cgctaagca ataactgtcg ttaactgctt tgttggtact   1800
acctgacttc accctcttt aagatgtctt atcctgagaa atttgaaggt atcgctattc   1860
aatcacacga agattggaaa aacccaaaga agacaaagta tgacccaaaa ccattttacg   1920
atcatgacat tgacattaag atcgaagcat gtggtgtctg cggtagtgat attcattgtg   1980
cagctggtca ttggggcaat atgaagatgc cgctagtcgt tggtcatgaa atcgttggta   2040
aagttgtcaa gctagggccc aagtcaaaca gtgggttgaa agtcggtcaa cgtgttggtg   2100
taggtgctca agtcttttca tgcttggaat gtgaccgttg taagaatgat aatgaaccat   2160
actgcaccaa gtttgttacc acatacagtc agccttatga agacggctat gtgtcgcagg   2220
gtggctatgc aaactacgtc agagttcatg aacattttgt ggtgcctatc ccagagaata   2280
ttccatcaca tttggctgct ccactattat gtggtggttt gactgtgtac tctccattgg   2340
ttcgtaacgg ttgcggtcca ggtaaaaag ttggtatagt tggtcttggt ggtatcggca   2400
gtatgggtac attgatttcc aaagccatgg gggcagagac gtatgttatt tctcgttctt   2460
cgagaaaaag agaagatgca atgaagatgg gcgccgatca ctacattgct acattagaag   2520
aaggtgattg gggtgaaaag tactttgaca ccttcgacct gattgtagtc tgtgcttcct   2580
cccttaccga cattgacttc aacattatgc caaaggctat gaaggttggt ggtagaattg   2640
tctcaatctc tataccagaa caacacgaaa tgttatcgct aaagccatat ggcttaaagg   2700
ctgtctccat ttcttacagt gctttaggtt ccatcaaaga attgaaccaa ctcttgaaat   2760
tagtctctga aaaagatatc aaaatttggg tggaaacatt acctgttggt gaagccggcg   2820
tccatgaagc cttcgaaagg atggaaaagg gtgacgttag atatagattt accttagtcg   2880
```

```
gctacgacaa agaattttca gactaggatc cataaaacga aaggctcagt cgaaagactg    2940
ggcctttcgt tttatctgtt gtttgtcggt gaacgctctc ctgagtagga caaatccgcc    3000
gggagcggat ttgaacgttg cgaagcaacg gcccggaggg tggcgggcag gacgcccgcc    3060
ataaactgcc aggcatcaaa ttaagcagaa ggccatcctg acggatggcc ttttgagctc    3120

<210> SEQ ID NO 4
<211> LENGTH: 3075
<212> TYPE: DNA
<213> ORGANISM: Artificial sequence
<220> FEATURE:
<223> OTHER INFORMATION: KDCa- ADH6 expression operon

<400> SEQUENCE: 4
actagttgtt gacaattaat catccggctc gtataatgtg tggaattgtg agcggataac      60
aatttcacac aggaaacaga ccatggctta tactgtgggg gattatttgt tggataggtt     120
gcatgaatta ggcatcgagg aaatctttgg tgtacctgga gattacaatt tgcaatttct     180
ggaccagatc atatcgagag aggatatgaa atggattggt aacgccaatg aattaaatgc     240
cagctatatg gccgatggct atgctcgtac caagaaagct gctgcttttc tgacaacttt     300
tggtgtcggt gaattgtctg ctattaacgg actggccggt agttatgctg aaaatttgcc     360
agtagttgaa atagtcggaa gcccaacttc taaagtgcaa aacgatggca aattcgtgca     420
tcatactctg gcagatggtg atttttaagca cttcatgaaa atgcatgaac ccgtaacggc     480
tgccagaact ctttttaacag ccgagaatgc gacatatgaa attgatcgtg tactttctca     540
gcttttaaag gagagaaaac ctgtttacat aaacttacct gtcgatgttg ctgctgccaa     600
agcagagaag ccagccctgt ctcttgaaaa agaaagctcc accaccaaca ctaccgaaca     660
agtgatatta tctaaaattg aggaatcact taaaaacgct cagaaaccag tagtcatagc     720
gggtcatgaa gtcataagtt tcggtcttga aaagactgta acacaatttg tcagcgaaac     780
aaaattgcct atcactactt tgaactttgg caaaagtgcg gtcgacgagt cgttgccatc     840
atttttgggt atctacaatg caaactatc agaaatctca ttgaaaaatt cgtagaaag     900 tgcggatttc attctgatgt tgggcgtcaa gctgacggat tcttctacgg gggctttcac     960
tcaccatttg gatgaaaaca aaatgatttc attgaacatc gatgaaggga tcatctttaa    1020
taaggtagtg gaagatttcg attttagagc cgtggtttcc tccttatcag agttaaaagg    1080
tattgagtac gaagggcagt atattgataa gcagtacgag gaatttattc cttcttctgc    1140
tccactttct caagatcgtt tatggcaagc agtcgagtcc ctgacacaaa gcaacgagac    1200
tatagttgca gagcaaggga cctcattctt tggtgcctct acaatttttc tgaaatccaa    1260
cagcagattt ataggacaac ccctttgggg ctctattgga tatactttttc ccgcagccct    1320 tggttcacaa atcgcagata aggagtcaag acatctgtta ttcataggtg atggtagtct    1380
acaattaaca gttcaagaat taggcctatc aataagggag aagttaaacc caatctgttt    1440
cataattaac aatgacggct acactgttga aagggagatc cacggaccaa cacaatcata    1500
caatgatatt cccatgtgga actatagcaa attaccggag actttcggcg caaccgagga    1560
tagagtagtt tcgaagatcg ttaggactga gaatgaattt gttagcgtta tgaaggaagc    1620
ccaggctgat gtcaatagaa tgtattggat tgaattagtt ttggaaaagg aagatgcacc    1680
taaattacta aaaagatgg ggaaactatt tgctgagcaa aacaaataac tgtcgttaac    1740
tgctttgttg gtactacctg acttcaccct cttttaagat gtcttatcct gagaaatttg    1800
aaggtatcgc tattcaatca cacgaagatt ggaaaaaccc aaagaagaca aagtatgacc    1860
```

```
caaaaccatt ttacgatcat gacattgaca ttaagatcga agcatgtggt gtctgcggta    1920
gtgatattca ttgtgcagct ggtcattggg gcaaatgaga gatgccgcta gtcgttggtc    1980
atgaaatcgt tggtaaagtt gtcaagctag ggcccaagtc aaacagtggg ttgaaagtcg    2040
gtcaacgtgt tggtgtaggt gctcaagtct tttcatgctt ggaatgtgac cgttgtaaga    2100
atgataatga accatactgc accaagtttg ttaccacata cagtcagcct tatgaagacg    2160
gctatgtgtc gcagggtggc tatgcaaact acgtcagagt tcatgaacat tttgtggtgc    2220
ctatcccaga gaatattcca tcacatttgg ctgctccact attatgtggt ggtttgactg    2280
tgtactctcc attggttcgt aacggttgcg gtccaggtaa aaaagttggt atagttggtc    2340
ttggtggtat cggcagtatg ggtacattga tttccaaagc catgggggca gagacgtatg    2400
ttatttctcg ttcttcgaga aaagagaag atgcaatgaa gatgggcgcc gatcactaca    2460
ttgctacatt agaagaaggt gattggggtg aaaagtactt tgacaccttc gacctgattg    2520
tagtctgtgc ttcctcccct accgacattg acttcaacat tatgccaaag gctatgaagg    2580
ttggtggtag aattgtctca atctctatac cagaacaaca cgaaatgtta tcgctaaagc    2640
catatggctt aaaggctgtc tccatttctt acagtgcttt aggttccatc aaagaattga    2700
accaactctt gaaattagtc tctgaaaaag atatcaaaat ttgggtggaa acattacctg    2760
ttggtgaagc cggcgtccat gaagccttcg aaaggatgga aaagggtgac gttagatata    2820
gatttacctt agtcggctac gacaaagaat tttcagacta ggatccataa aacgaaaggc    2880
tcagtcgaaa gactgggcct ttcgttttat ctgttgtttg tcggtgaacg ctctcctgag    2940
taggacaaat ccgccgggag cggatttgaa cgttgcgaag caacggcccg gagggtggcg    3000
ggcaggacgc ccgccataaa ctgccaggca tcaaattaag cagaaggcca tcctgacgga    3060 tggcctttg agctc                                                    3075

<210> SEQ ID NO 5
<211> LENGTH: 35
<212> TYPE: DNA
<213> ORGANISM: Artificial sequence
<220> FEATURE:
<223> OTHER INFORMATION: Primer ilvB-5

<400> SEQUENCE: 5
gttgcacatg ttagggcaaa tgaacaccgc agacc                              35

<210> SEQ ID NO 6
<211> LENGTH: 44
<212> TYPE: DNA
<213> ORGANISM: Artificial sequence
<220> FEATURE:
<223> OTHER INFORMATION: Primer ilvB-3

<400> SEQUENCE: 6
ctacgttaac gacagagatc tttattccca aatttcacag gcca                    44

<210> SEQ ID NO 7
<211> LENGTH: 1836
<212> TYPE: DNA
<213> ORGANISM: Artificial sequence
<220> FEATURE:
<223> OTHER INFORMATION: ilvB expression cassette

<400> SEQUENCE: 7
actagtcctg aggtgttgac aattaatcat ccggctcgta taatgtgtgg aattgtgagc    60
```

-continued

| | |
|---|---|
| ggataacaat ttcacacagg aaacagacca tgttagggca aatgaacacc gcagacctat | 120 |
| tggttcaatg tctggaaaat gaggacgttg aatacatttt tggcgtaccc ggagaggaaa | 180 |
| acctccacat cctcgaagcg ctgaaaaact cgcccatccg ctttattacc acccgccacg | 240 |
| aacagggagc agcctttatg ccgacgtttt acggccgttt aacgggcaaa gcggggttt | 300 |
| gtctttccac cctggggcct ggagccacca acctgatgac cggggtagcg gatgctaact | 360 |
| tggacggagc gcccctggtg gccatcactg gacaggtggg cacagatcgg atgcacatcg | 420 |
| aatcccacca atacctggac ttggtggcca tgttcgaccc ggtgactaaa tggaccaggc | 480 |
| aaattgtccg ccccagcatt accccggaag tggttcgtaa agcgttcaaa ttggctcaga | 540 |
| gcgaaaaacc aggggccacc cacattgatt taccagaaaa tattgccgct atgccggtgg | 600 |
| atgggaaacc cctacggcgg gacagtcggg aaaaggttta tgcagctttt cgtactttgg | 660 |
| gcacagcggc caacgccatt tccaaggcca aaaaccccat tattctggcc ggcaatggca | 720 |
| ccatccgagc cgaagccagc gaagccctga cggaatttgc caccagtttg aatattcccg | 780 |
| tggccaacac cttcatgggt aaaggcacca tgccctacac ccatcccctt tccctttgga | 840 |
| cagtgggctt acaacaacgg atcacatta cctgtgcctt tgaaaaaagc gatttggtca | 900 |
| ttgcggtggg ctatgactta attgaatatt ctccgaaaaa atggaatccc actggagatt | 960 |
| tgcccatcat tcacattggc gctactccgg cggaaattga tagcagttat attccccagg | 1020 |
| tggaggtggt gggggacatt accgattccc tgatggattt gctcaaacgg tgcgatcgcc | 1080 |
| aaggtaaacc cactccctac ggggcttctc tccgggcgga aattcgggcc gagtatgaat | 1140 |
| gttatgccaa tgcacaggt tttcccgtta agccacaaaa aattatttat gacctgcgcc | 1200 |
| aagtgatggg ccccgatgat gtggtgattt ccgatgtggg ggcccataaa atgtggatgg | 1260 |
| cccgccatta ccactgtgac agccccaaca cctgtttaat ttccaatggt tttgcggcca | 1320 |
| tgggcattgc cattccaggg gcgatcgccg ctaagctggt ttatcctgag cgcaacattg | 1380 |
| ttgcagtgac gggggacggc ggtttttatga tgaactgtca ggagttggaa acggccatgc | 1440 |
| gggtgggcac tccctttgtc acgttgattt ttaacgacaa cggttacggc ctaattgagt | 1500 |
| ggaaacagat caaccaattt ggcgaatcca gctttattaa atttggcaat ccagactttg | 1560 |
| ttaagtttgc tgaaagtatg ggtctcaaag gttatcgggt ggaagcggcg gcggatttaa | 1620 |
| ttcctatcct caaagaagct ttagctcaac ctgtgcccac agtgattgat tgtcctgtgg | 1680 |
| attatcggga gaatattcgt ttctcgcaaa aagcagggga attggcctgt gaaatttggg | 1740 |
| aataaagatc tgatccgctg ttgacccaac agcatgagtc gttatccaag gggagcttcg | 1800 |
| gctccctttt ttcatgcgcg gatgcggtga gagctc | 1836 |

<210> SEQ ID NO 8
<211> LENGTH: 623
<212> TYPE: PRT
<213> ORGANISM: Pichia stipitis

<400> SEQUENCE: 8

Met Thr Pro Val Gln Glu Thr Ile Arg Leu Pro Gly Thr Ser Ser Pro
1               5                   10                  15

Thr Val Pro Glu Asn Val Thr Leu Gly Glu Tyr Leu Phe Leu Arg Ile
            20                  25                  30

Ser Gln Ala Asn Pro Lys Leu Arg Ser Ile Phe Gly Ile Pro Gly Asp
        35                  40                  45

Phe Asn Val Asp Leu Leu Glu His Leu Tyr Ser Pro Val Val Ala Gly
    50                  55                  60

```
Arg Asp Ile Lys Phe Ile Gly Leu Cys Asn Glu Leu Asn Gly Ala Tyr
 65                  70                  75                  80

Thr Ala Asp Gly Tyr Ser Arg Ala Ile Gly Leu Ser Thr Phe Ile
             85                  90                  95

Ser Thr Phe Gly Val Gly Glu Leu Ser Ala Ile Asn Gly Ile Ala Gly
            100                 105                 110

Ser Phe Ala Glu Phe Ser Pro Val Leu His Ile Val Gly Thr Thr Ser
            115                 120                 125

Leu Pro Gln Arg Asp His Ala Ile Asn Gly Ser Asp Val Arg Asn His
        130                 135                 140

His His Leu Ile Gln Asn Lys Asn Pro Leu Cys Gln Pro Asn His Asp
145                 150                 155                 160

Val Tyr Lys Lys Met Ile Glu Pro Ile Ser Val Ile Gln Glu Ser Leu
                165                 170                 175

Asp Ser Asp Leu Gln Arg Asn Met Glu Lys Ile Asp Arg Val Leu Val
            180                 185                 190

Lys Ile Leu Gln Glu Ser Arg Pro Gly Tyr Leu Phe Ile Pro Cys Asp
        195                 200                 205

Ile Thr Asn Leu Ile Val Pro Ser Tyr Arg Leu Tyr Glu Thr Pro Leu
210                 215                 220

Pro Leu Glu Ile Gln Leu Thr Thr Ser Gly Val Glu Val Leu Glu Asp
225                 230                 235                 240

Val Val Asp Ala Ile Leu Phe Arg Leu Tyr Lys Ser Lys Asn Pro Ser
                245                 250                 255

Leu Leu Ser Asp Cys Leu Thr Thr Arg Phe Asn Leu Gln Asp Lys Leu
            260                 265                 270

Asn Thr Leu Val Ala Lys Leu Pro Ser Asn Phe Val Lys Leu Phe Ser
        275                 280                 285

Thr Asn Met Ala Arg Asn Ile Asp Glu Ser Leu Ser Asn Phe Val Gly
        290                 295                 300

Leu Tyr Phe Gly Ile Gly Ser Ser Ser Lys Glu Val Ser Arg Gln Leu
305                 310                 315                 320

Glu Arg Asn Thr Asp Phe Leu Ile Asn Leu Gly Tyr Phe Asn Ala Glu
                325                 330                 335

Thr Thr Thr Ala Gly Tyr Ser Asn Asp Phe Ser Asn Ile Glu Glu Tyr
            340                 345                 350

Ile Glu Ile Asn Pro Asp Tyr Ile Lys Val Asn Glu His Ile Ile Asn
        355                 360                 365

Ile Lys Asn Pro Glu Ser Gly Lys Arg Leu Phe Ser Met Gly Gln Leu
        370                 375                 380

Leu Asp Ala Leu Leu Phe Lys Leu Asp Leu Asn Lys Ile Glu Asn Ile
385                 390                 395                 400

Asn Asn Asn Asn Ile Ser Tyr Lys Phe Phe Pro Pro Thr Leu Tyr Glu
                405                 410                 415

Gln Asp Asn Asn Thr Asp Tyr Ile Pro Gln Thr Lys Leu Val Asp Tyr
            420                 425                 430

Leu Asn Glu Asn Leu Gln Pro Gly Asp Leu Leu Val Met Asp Thr Met
        435                 440                 445

Ser Phe Cys Phe Ala Leu Pro Asp Ile Met Leu Pro Gln Gly Val Gln
        450                 455                 460

Leu Leu Thr Gln Asn Tyr Tyr Gly Ser Ile Gly Tyr Ala Leu Pro Ser
465                 470                 475                 480
```

```
Thr Phe Gly Ala Thr Met Ala Val Asn Asp Leu Gly Ser Asp Arg Arg
                485             490                 495
Ile Ile Leu Ile Glu Gly Asp Gly Ala Ala Gln Met Thr Ile Gln Glu
            500             505                 510
Leu Ser Ser Phe Leu Lys Tyr Lys Glu Phe Leu Pro Asn Met Pro Lys
        515             520                 525
Ile Phe Leu Ile Asn Asn Asp Gly Tyr Thr Val Glu Arg Met Ile Lys
        530             535             540
Gly Pro Thr Arg Ser Tyr Asn Asp Ile Asn Gly Glu Trp Ser Trp Thr
545             550                 555                 560
Gln Leu Leu Gly Val Phe Gly Asp Lys Glu Gln Lys Tyr His Ser Thr
                565             570                 575
Ala Leu Leu Arg Asn Val Asn Glu Phe Asn Lys Tyr Phe Glu Phe Gln
            580             585                 590
Arg Gln Thr Asp Asn Ser Lys Leu Glu Phe Ile Glu Leu Ile Ala Gly
        595             600             605
Lys Tyr Asp Cys Pro Leu Arg Phe Ser Glu Met Phe Cys Lys Lys
        610             615             620
```

PRODUCTION OF BRANCHED-CHAIN ALCOHOLS BY PHOTOSYNTHETIC MICROORGANISMS

CROSS REFERENCE TO RELATED APPLICATIONS

This application is a continuation application of U.S. application Ser. No. 13/338,579 filed Dec. 28, 2011, now issued as U.S. Pat. No. 8,445,257; which is a continuation application of U.S. application Ser. No. 12/635,653 filed Dec. 10, 2009, now issued as U.S. Pat. No. 8,124,400; which claims the benefit under 35 USC §119(e) to U.S. Application Ser. No. 61/121,522 filed Dec. 10, 2008, now expired. The disclosure of each of the prior applications is considered part of and is incorporated by reference in the disclosure of this application.

BACKGROUND OF THE INVENTION

1. Field of the Invention

The present invention provides genes, polypeptides, and expression constructs therefor, recombinant photosynthetic microorganisms and methods of uses therefor, such as the production of branched-chain alcohols, which can optionally be derivatized to produce further compounds. This biological route provides advantages over other known methods of production.

INCORPORATION BY REFERENCE OF SEQUENCE LISTING

This application contains references to amino acid sequences and/or nucleic acid sequences which have been submitted concurrently herewith as the sequence listing text file "SGI1220-3_ST25.txt", file size 25.0 KiloBytes (KB), created on May 20, 2013. The aforementioned sequence listing is hereby incorporated by reference in its entirety pursuant to 37 C.F.R. §1.52(e)(5).

2. Background Information

Branched-chain alcohols and their derivatives have a variety of utilities that are known in the art, for example, as fuels, fuel additives, and solvents. Advantages of using branched-chain alcohols such as isobutanol, 2-methyl-1-butanol, and 3-methyl-1-butanol as fuels or fuel additives include an energy content higher than that of ethanol and their ability to be transported using existing fuel pipelines. Traditional methods for the production of branched-chain alcohols are costly, for example fermentation requires a fermentable carbon source, typically a sugar or polysaccharide, which adds to the cost of production.

US 2007/0092957 discloses synthesis of isobutanol by recombinant nonphotosynthetic bacteria and yeast that utilize glucose or sucrose as carbon sources. US 2007/0259411 describes the selection of butanol-tolerant bacterial *Enterococcus* species in a growth medium that includes a fermentable carbon source for the production of alcohols. US 2008/0261230 provides genes encoding high activity keto-acid reductoisomerases that can be used to genetically engineer microorganisms for the production of isobutanol. US 2009/0081746 discloses the synthesis of branched-chain alcohols including isobutanol, 1-butanol, 1-propanol, 2-methyl 1-butanol, 3-methyl-1-butanol, and 2-phenylethanol by recombinant *E. coli* strains in cultures that include glucose.

US 2009/0288337 (application Ser. No. 12/332,305) and WO 20009/076480 (PCT application US2008/086296), both incorporated by reference herein, describe genetically engineered microorganisms such as bacteria and yeast for the synthesis of 2-methyl-1-butanol.

SUMMARY OF THE INVENTION

This invention provides polypeptides, genes, expression constructs, metabolic pathways, strains of photosynthetic microorganisms, and methods to biologically produce branched-chain alcohols, including, for example, 2-methyl-1-butanol, 3-methyl-1-butanol, and isobutanol.

One aspect of this invention involves the production of recombinant photosynthetic microorganisms via introduction of heterologous genes that encode enzymes that enhance the production and decarboxylation of 2-keto branched-chain acids, leading to the production of the corresponding branched-chain aldehydes. Additional gene introductions can then be carried out to enable the efficient reduction of the branched-chain aldehydes to the corresponding branched-chain alcohols. In addition, the invention provides methods where branched-chain alcohols are enzymatically dehydrated in vivo to produce various branched-chain alpha-olefins.

In one embodiment, the invention provides a recombinant photosynthetic microorganism that includes at least one heterologous DNA sequence encoding at least one polypeptide that catalyzes a substrate to product conversion that leads to the synthesis of isobutanol. The encoded polypeptide can be a polypeptide that catalyzes the conversion of: (1) pyruvate to 2-hydroxy-2-methyl-3-oxobutanoate; (2) 2-hydroxy-2-methyl-3-oxobutanoate to 2,3-dihydroxy-3-methylbutanoate; (3) 2,3-dihydroxy-3-methylbutanoate to 3-methyl-2-oxobutanoate; (4) 3-methyl-2-oxobutanoate to 2-methyl-1-propanal; or (5) 2-methyl-1-propanal to 2-methyl-1-propanol (isobutanol).

In another embodiment, the invention provides a recombinant photosynthetic microorganism that includes at least one heterologous DNA sequence encoding at least one polypeptide that catalyzes a substrate to product conversion selected that leads to the synthesis of 2-methyl-1-butanol. The encoded polypeptide can be a polypeptide that catalyzes the conversion of: (6) pyruvate to 2-methylmalate; (7) 2-methylmalate to 2-methylmaleate; (8) 2-methylmaleate to D-erythro-3-methylmalate; (9) D-erythro-3-methylmalate to 2-oxobutanoate; (10) threonine to 2-oxobutanoate; (11) pyruvate and 2-oxobutanoate to 2-hydroxy-2-ethyl-3-oxobutanoate; (12) 2-hydroxy-2-ethyl-3-oxobutanoate to 2,3-dihydroxy-3-methylpentanoate; (13) 2,3-dihydroxy-3-methylpentanoate to 3-methyl-2-oxopentanoate; (14) 3-methyl-2-oxopentanoate to 2-methyl-1-butanal; and (15) 2-methyl-1-butanal to 2-methyl-1-butanol.

In another embodiment, the invention provides a recombinant photosynthetic microorganism that includes at least one heterologous DNA sequence encoding at least one polypeptide that catalyzes a substrate to product conversion that leads to the synthesis of 3-methyl-1-butanol. The encoded polypeptide can be a polypeptide that catalyzes the conversion of: (16) pyruvate to 2-hydroxy-2-methyl-3-oxobutanoate; (17) 2-hydroxy-2-methyl-3-oxobutanoate to 2,3-dihydroxy-3-methylbutanoate; (18) 2,3-dihydroxy-3-methylbutanoate to 3-methyl-2-oxobutanoate; (19) 3-methyl-2-oxobutanoate to 2-isopropylmalate; (20) 2-isopropylmalate to 2-isopropylmaleate; (21) 2-isopropylmaleate to 3-isopropylmalate; (22) 3-isopropylmalate to 4-methyl-2-oxopentanoate (2-ketoisocaproate); (23) 4-methyl-2-oxopentanoate to 3-methyl-1-butanal; and (24) 3-methyl-1-butanal to 3-methyl-1-butanol.

In some embodiments, provided herein are recombinant photosynthetic microorganisms that include a heterologous nucleic acid molecule that encodes a branched-chain 2-ketoacid decarboxylase, in which the photosynthetic microorganism produces a branched-chain alcohol such as isobutanol, 2-methyl-1-butanol, or 3-methyl-1-butanol. In an exemplary embodiment, a photosynthetic microorganism comprises a heterologous nucleic acid sequence encoding kdcA of *Lactococcus lactis* or a variant thereof. In another exemplary embodiment, a photosynthetic microorganism comprises a heterologous nucleic acid sequence encoding PDC3-6 of *Pichia stipilis* or a variant thereof.

In some embodiments, recombinant photosynthetic microorganisms are provided that produce one or more branched-chain alcohols, in which the photosynthetic microorganisms include a heterologous nucleic acid sequence encoding an alcohol dehydrogenase, such as a branched-chain alcohol dehydrogenase. In an exemplary embodiment, a recombinant photosynthetic microorganism includes a heterologous nucleic acid sequence encoding ADH6 of *Saccharomyces cerevisa*, or a variant thereof.

In further embodiments, a recombinant photosynthetic microorganism is genetically engineered for the production of one or more branched-chain alcohols, such as isobutanol, 2-methyl-1-butanol, or 3-methyl-1 butanol, includes at least one heterologous nucleic acid sequence encoding one or more enzymes selected from the group consisting of an acetolactate synthase (EC 2.2.1.6), a ketol-acid reductoisomerase (EC 1.1.1.86), or dihydroxyacid dehydratase (EC 4.2.1.9). In some exemplary embodiments, a recombinant photosynthetic microorganism includes a heterologous nucleic acid sequence encoding an acetolactate synthase (EC 2.2.1.6).

Recombinant photosynthetic microorganisms in certain embodiments of the invention are engineered to produce 3-methyl-1-butanol and include one or more heterologous nucleic acid sequences encoding one or more of the enzymes 2-isopropylmalate synthase (EC 2.3.3.13), 3-isopropylmalate dehydratase (EC 4.2.1.33), or 3-isopropylmalate dehydrogenase (EC 1.1.1.85).

In other embodiments, a recombinant photosynthetic microorganism is genetically engineered to produce 2-methyl-1-butanol, and includes at least one heterologous nucleic acid sequence encoding one or more of the enzymes homoserine dehydrogenase (EC 1.1.1.3), homoserine kinase (EC 2.7.1.39), threonine synthase (EC 4.2.3.1), or threonine ammonia-lyase (EC 4.3.1.19).

A further aspect of the invention is a method for producing a branched-chain alcohol in which the method includes culturing a recombinant photosynthetic microorganism as provided herein, such as a microorganism that includes a heterologous sequence encoding a branched-chain 2-ketoacid decarboxylase and a heterologous sequence encoding an alcohol dehydrogenase, to produce a branched-chain alcohol. In some preferred embodiments the photosynthetic microorganism is cultured photoautotrophically. In some embodiments, the photosynthetic microorganism is cultured in the absence of a reduced carbon source, such as a sugar or organic acid. The photosynthetic microorganism culture is in some embodiments provided with inorganic carbon such as $CO_2$, carbonic acid, or a carbonate salt.

A photosynthetic microorganism used in the methods may further include at least one heterologous nucleic acid sequence encoding one or more of an acetolactate synthase (EC 2.2.1.6), a ketol-acid reductoisomerase (EC 1.1.1.86), or dihydroxyacid dehydratase (EC 4.2.1.9). A branched-chain alcohol produced by the culture is in some preferred embodiments isobutanol, 2-methyl-1-butanol, or 3-methyl-1-butanol.

In some embodiments, the photosynthetic microorganism produces 3-methyl-1-butanol. In some embodiments, the photosynthetic microorganism produces 3-methyl-1-butanol and is engineered to include at least one heterologous nucleic acid sequence encoding one or more of the enzymes 2-isopropylmalate synthase (EC 2.3.3.13), 3-isopropylmalate dehydratase (EC 4.2.1.33), or 3-isopropylmalate dehydrogenase (EC 1.1.1.85).

In some embodiments, the photosynthetic microorganism produces 2-methyl-1-butanol. In some embodiments, the photosynthetic microorganism produces 2-methyl-1-butanol and is engineered to include at least one nucleic acid sequence encoding one or more of the enzymes homoserine dehydrogenase (EC 1.1.1.3), homoserine kinase (EC 2.7.1.39), threonine synthase (EC 4.2.3.1), or threonine ammonia-lyase (EC 4.3.1.19).

In some embodiments, the method includes recovering the branched-Chain alcohol from the culture medium, for example, using methods such as distillation, liquid-liquid extraction, gas stripping, steam stripping, and/or pervaporation.

In another aspect, included within the scope of the invention is a branched-chain alcohol made by the methods provided herein. The branched-chain alcohol produced by a recombinant photosynthetic microorganism can be, for example, isobutanol, 2-methyl-1-butanol, or 3-methyl-1-butanol.

BRIEF DESCRIPTION OF THE DRAWINGS

FIG. 3 provides SEQ ID NO:1, the sequence of an operon for expression in *Synechococcus elongatus* including codon-optimized *Saccharomyces cerevisiae* pyruvate decarboxylase gene PDC1, the *S. elongatus* KaiBC intergenic region, the codon-optimized *S. cerevisiae* alcohol dehydrogenase gene ADH2, and the rrnB terminator.

FIG. 4 provides SEQ ID NO:2, the sequence of an operon for expression in *Synechococcus elongatus* including a 2-ketoacid decarboxylase gene from *Lactococcus lactis* (KDCa) in combination with a codon-optimized *S. cerevisiae* ADH2 gene.

FIG. 5 provides SEQ ID NO:3, the sequence of an operon including the *S. cerevisiae* ADH6 gene in combination with the codon-optimized *S. cerevisiae* PDC1 gene.

FIG. 6 provides SEQ ID NO:4, the sequence of an operon including the *L. lactis* KDCa gene in combination with the *S. cerevisiae* ADH6 gene.

FIG. 7 provides SEQ ID NO:7, the sequence of an expression construct that includes the trc promoter, and the *Synechocystis* sp. PCC 6803 ilvB coding sequence and the rps14 terminator.

FIG. 8 provides SEQ ID NO:8, the sequence of the branched-chain 2-ketoacid decarboxylase protein encoded by the PDC3-6 gene of *Pichia stipitis*.

DETAILED DESCRIPTION OF THE INVENTION

Figure 1:
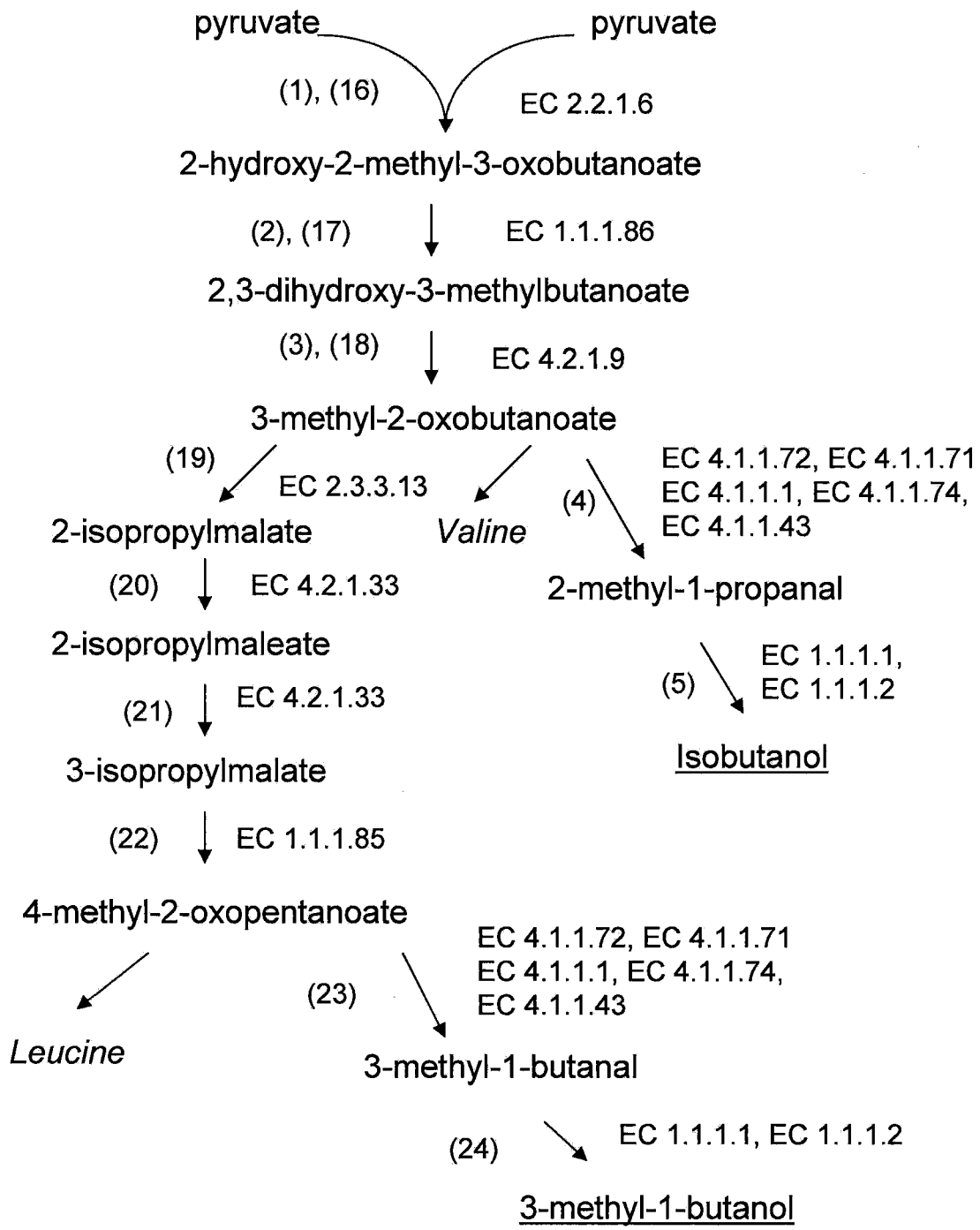
FIG. 1 depicts a biochemical pathway for the synthesis of isobutanol that overlaps with the biosynthetic pathway for the amino acid valine and a biochemical pathway for the synthesis of 3-methyl-1-butanol that overlaps with the biosynthetic pathway for the amino acid leucine.

This application incorporates by reference U.S. patent application Ser. No. 12/332,305; PCT application PCT/US08/086,296; and U.S. provisional application 60/012,749 in their entireties.

All publications and patent applications mentioned in this specification are herein incorporated by reference to the same extent as if each individual publication or patent application was specifically and individually indicated to be incorporated by reference.

Unless defined otherwise, all technical and scientific terms used herein have the same meaning as commonly understood by one of ordinary skill in the art to which this invention is related. The following terms are defined for purposes of the invention as described herein.

The singular form "a", "an" and "the" include plural referents unless the context clearly dictates otherwise. Thus, for example, reference to "a cell" includes a plurality of cells and reference to "an antibody" includes a plurality of antibodies, etc.

As used herein, the terms "about" or "approximately" when referring to any numerical value are intended to mean a value of plus or minus 10% of the stated value. For example, "about 50 degrees C" (or "approximately 50 degrees C") encompasses a range of temperatures from 45 degrees C. to 55 degrees C., inclusive. Similarly, "about 100 mM" (or "approximately 100 mM") encompasses a range of concentrations from 90 mM to 110 mM, inclusive. All ranges provided within the application are inclusive of the values of the upper and lower ends of the range.

An "isolated" biomolecule such as an isolated protein or nucleic acid, is a biomolecule removed from the context in which the biomolecule exist in nature. For example, an isolated protein or nucleic acid molecule is removed from the cell or organism with which it is associated in its natural state. An isolated biomolecule can be, in some instances, partially or substantially purified, for example, an isolated nucleic acid molecule can be a nucleic acid sequence that has been excised from the chromosome, genome, or episome that it is integrated into in nature.

A recombinant or "engineered" nucleic acid molecule is a nucleic acid molecule that has been altered through human intervention. As nonlimiting examples, a recombinant nucleic acid molecule: 1) includes conjoined nucleotide sequences that are not conjoined in nature, 2) has been engineered using molecular cloning techniques such that it lacks one or more nucleotides with respect to the naturally occurring nucleic acid molecule sequence, or 3) has been manipulated using molecular cloning techniques such that it has one or more sequence changes or rearrangements with respect to the naturally occurring nucleic acid sequence. As nonlimiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

A recombinant or "engineered" organism is an organism into which one or more recombinant or "engineered" nucleic acid molecules has been introduced.

A "homolog" of a gene or protein refers to its functional equivalent in another species.

A "variant" of a gene or nucleic acid sequence is a sequence having at least 65% identity with the referenced gene or nucleic acid sequence, and can include one or more base deletions, additions, or substitutions with respect to the referenced sequence. Variants also include chimeric genes that include sequences from two or more sources. Variants also include codon-optimized genes, and genes containing mutations, insertions, deletions, or substitutions, either naturally-occurring or recombinant. A variant can be a naturally-occurring variant or the result of a spontaneous or induced mutation. Induced mutations can be created using methods known in the art for mutagenesis of organisms or cells (for example, using gamma or UV irradiation or chemical mutagens such as 5-bromo deoxyuridine, ethyl methane sulfonate (EMS), methyl methane sulfonate (MMS), diethylsulfate (DES), nitrosoguanidine (NTG), ICR compounds, etc., or can be introduced using genetic engineering techniques, such as gene synthesis, in vivo single strand repair techniques, polymerase-based amplification at error-permissive temperature and/or polymerase-based amplification using primers that incorporate base changes.

A "variant" of a peptide or protein is a peptide or protein sequence that varies at one or more amino acid positions with respect to the reference peptide or protein. A variant can be a naturally-occurring variant or can be the result of spontaneous, induced, or genetically engineered mutation(s) to the nucleic acid molecule encoding the variant peptide or protein. A variant peptide can also be a chemically synthesized variant.

The degree of amino acid or nucleic acid sequence identity can be determined by various computer programs for aligning the sequences to be compared based on designated program parameters. For example, sequences can be aligned and compared using the local homology algorithm of Smith & Waterman, Adv. Appl. Math. 2:482 (1981), the homology alignment algorithm of Needleman & Wunsch, J. Mol. Biol. 48:443 (1970), or the search for similarity method of Pearson & Lipman, Proc. Nat'l. Acad. Sci. USA 85:2444 (1988), and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

The BLAST algorithm, described in Altschul et al., J. Mol. Biol. 215:403-410 (1990), is publicly available through software provided by the National Center for Biotechnology Information (at the web address www.ncbi.nlm.nih.gov). This algorithm identifies high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). Initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=−4; and a comparison of both strands. The TBLASTN program (using a protein sequence to query nucleotide sequence databases) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

"Exogenous" in the context of a gene or protein is a gene or protein that is not derived from the host organism species.

A "heterologous" gene or nucleic acid sequence is a gene or sequence from a different source than the host organism it is introduced into, or from a different source than another nucleic acid sequence with which is juxtaposed in a nucleic acid construct. For example, a gene of one species introduced into another species may be referred to as a heterologous gene. A nucleic acid molecule that includes a gene operably linked to a promoter that is not the natural promoter for the gene (not the promoter linked to the gene in its natural state) is also referred to herein as a heterologous nucleic acid molecule or sequence, even though the gene may be derived from the same species as the host organism.

A gene that is "codon-optimized" for expression in an organism is a gene whose nucleotide sequence has been altered with respect to the original nucleotide sequence, such that one or more codons of the nucleotide sequence has been changed to a different codon that encodes the same amino acid, in which the new codon is used more frequently in genes of the organism of interest than the original codon. The degeneracy of the genetic code provides that all amino acids except form methionine and tryptophan are encoded by more than one codon. For example, arginine, leucine, and serine are encoded by different six different codons; glycine, alanine, valine, threonine, and proline are encoded by four different codons. Many organisms use certain codons to encode a particular amino acid more frequently than others. Without limiting any aspects of the invention to any particular mechanism, it is believed that some tRNAs for a given amino acid are more prevalent than others within a particular organism, and genes requiring a rare tRNA for translation of the encoded protein may be expressed at a low level due in part to a limiting amount of the rare tRNA. Thus, for adequate or optimal levels of expression of an encoded protein, a gene may be "codon-optimized" to change one or more codons to new codons ("preferred codons") that are among those used more frequently in the genes of the host organism (referred to as the "codon preference" of the organism). As used in the context of the invention, a "codon-optimized" gene or nucleic acid molecule of the invention need not have every codon altered to conform to the codon preference of the intended host organism, nor is it required that altered codons of a "codon-optimized" gene or nucleic acid molecule be changed to the most prevalent codon used by the organism of interest. For example, a codon-optimized gene may have one or more codons changed to codons that are used more frequently that the original codon(s), whether or not they are used most frequently in the organism to encode a particular amino acid.

A "photosynthetic microorganism" is any prokaryotic or eukaryotic single-celled or colonial organism that can perform photosynthesis and that can be seen as a single organism only with the aid of a microscope. Photosynthetic microorganisms include eukaryotic microalgae and photosynthetic bacteria. Eukaryotic microalgae include species of green algae (Chlorophyceae), yellow-green algae (Xanthophyceae), golden algae (Chrysophyceae), brown algae (Phaeophyceae), red algae (Rhodophyceae), diatoms (Bacillariophyceae), and "pico-plankton" (Prasinophyceae and Eustigmatophyceae). Photosynthetic bacteria include cyanobacteria, green sulfur bacteria, purple sulfur bacteria, purple nonsulfur bacteria, and green nonsulfur bacteria.

Photoautotrophic growth or culture means the growth of organisms in the absence of a supplied compound or molecule that can be metabolized for energy (such as a reduced carbon source) and under conditions in which the organisms use light as the sole energy source.

Inorganic carbon is carbon provided in a molecule that cannot itself be metabolized for energy by an organism, such as $CO_2$, carbonic acid, and carbonate. Sources of inorganic carbon include $CO_2$, air, carbonic acid, carbonate salts, and emissions such as flue gas.

Carbon dioxide (which, along with carbonic acid, bicarbonate and/or carbonate define the term "inorganic carbon") is converted in the photosynthetic process to organic compounds. The inorganic carbon source includes any way of delivering inorganic carbon, optionally in admixture with any other combination of compounds which do not serve as the primary carbon feedstock, but only as a mixture or carrier (for example, emissions from biofuel (e.g., ethanol) plants, power plants, petroleum-based refineries, as well as atmospheric and subterranean sources).

A reduced or organic carbon source is a carbon based molecule that can be metabolized by an organism for energy such as, for example, a carbohydrate (including a sugar or polysaccharide), amino acid, protein, organic acid, fatty acid, lipid, acetyl CoA, or any biosynthetic precurosor of any of these biomolecules.

Elements of the embodiments described herein can be combined to make additional embodiments not specifically described that are also within the scope of the invention. Headings within the application are solely for the convenience of the reader, and do not limit in any way the scope of the invention or its embodiments.

In one aspect, the invention includes engineering a recombinant photosynthetic microorganism to produce various branched-chain alcohol molecules. In preferred embodiments, the branched-chain alcohols the photosynthetic microorganisms are engineered to produce are five carbon branched-chain alcohols that can be synthesized using, in part, enzymes that catalyze substrate to product conversions on certain amino acid biosynthesis pathways.

Figure 2:
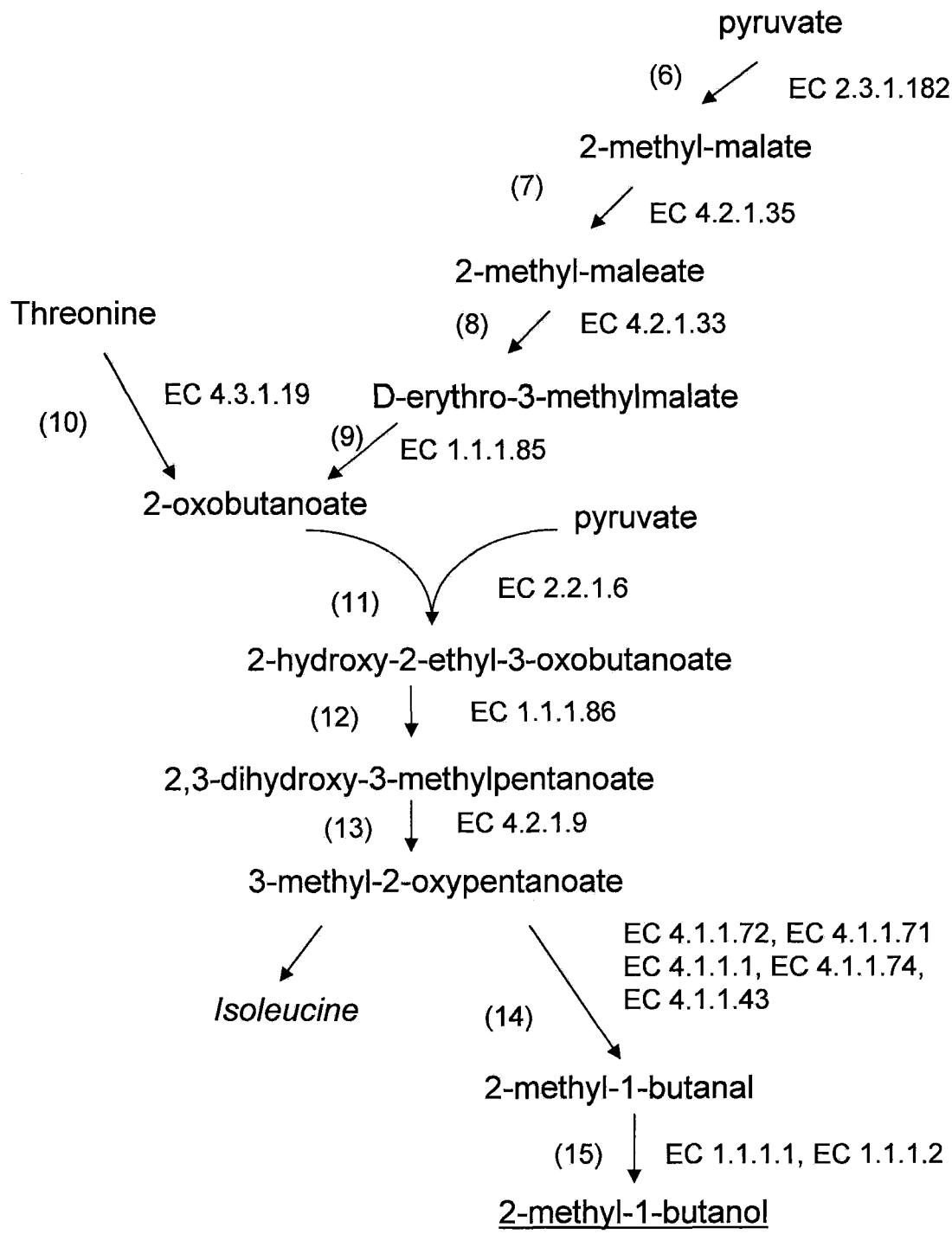
FIG. 2 depicts a biochemical pathway 2-methyl-1-butanol that overlaps with the biosynthetic pathway for the amino acid isoleucine.

One embodiment of this invention is to express in a photosynthetic microorganism one or more heterologous genes that encode enzymes involved in the production of branched-chain alcohols including isobutanol, 2-methyl-1-butanol, and 3-methyl-1-butanol. The synthesis of each of these products utilizes enzymes of an endogenous amino acid biosynthesis pathway. The recombinant microorganisms are engineered to include one or more heterologous genes encoding enzymes which, in combination with endogenous enzymes, result in synthesis of the branched-chain alcohols. Amino acid biosynthesis pathways for producing isoleucine, valine, and leucine, as well as additional enzymes for the production of isobutanol, 2-methyl-1-butanol, and 3-methyl-1-butanol that are not part of the endogenous amino acid pathways, are provided in FIGS. 1 and 2.

In one embodiment, the present invention provides methods of producing isobutanol. Each step of the enzymatic pathway is provided with a numeric designation which corresponds to an polypeptide with enzymatic activity to perform the following substrate to product conversions (FIG. 1):
(1) pyruvate to 2-hydroxy-2-methyl-3-oxobutanoate;
(2) 2-hydroxy-2-methyl-3-oxobutanoate to 2,3-dihydroxy-3-methylbutanoate;
(3) 2,3-dihydroxy-3-methylbutanoate to 3-methyl-2-oxobutanoate;
(4) 3-methyl-2-oxobutanoate to 2-methyl-1-propanal; and
(5) 2-methyl-1-propanal to 2-methyl-1-propanol (or isobutanol).

In another embodiment, the present invention provides methods of producing 2-methyl-1-butanol. Each step of the enzymatic pathway is provided with a numeric designation which corresponds to an polypeptide with enzymatic activity to perform the following substrate to product conversions (FIG. 2):
(6) pyruvate to 2-methylmalate;
(7) 2-methylmalate to 2-methylmaleate;
(8) 2-methylmaleate to D-erythro-3-methylmalate;
(9) D-erythro-3-methylmalate to 2-oxobutanoate;
(10) threonine to 2-oxobutanoate;
(11) Pyruvate and 2-oxobutanoate to 2-hydroxy-2-ethyl-3-oxobutanoate;
(12) 2-hydroxy-2-ethyl-3-oxobutanoate to 2,3-dihydroxy-3-methylpentanoate;
(13) 2,3-dihydroxy-3-methylpentanoate to 3-methyl-2-oxopentanoate;
(14) 3-methyl-2-oxopentanoate to 2-methyl-1-butanal; and
(15) 2-methyl-1-butanal to 2-methyl-1-butanol.

In another embodiment, the present invention provides methods of producing 3-methyl-1-butanol. Each step of the enzymatic pathway is provided with a numeric designation which corresponds to an polypeptide with enzymatic activity to perform the following substrate to product conversions (FIG. 1):
(16) pyruvate to 2-hydroxy-2-methyl-3-oxobutanoate;
(17) 2-hydroxy-2-methyl-3-oxobutanoate to 2,3-dihydroxy-3-methylbutanoate;
(18) 2,3-dihydroxy-3-methylbutanoate to 3-methyl-2-oxobutanoate;
(19) 3-methyl-2-oxobutanoate to 2-isopropylmalate;
(20) 2-isopropylmalate to 2-isopropylmaleate;
(21) 2-isopropylmaleate to 3-isopropylmalate;
(22). 3-isopropylmalate to 4-methyl-2-oxopentanoate (2-ketoisocaproate);
(23) 4-methyl-2-oxopentanoate to 3-methyl-1-butanal; and
(24) 3-methyl-1-butanal to 3-methyl-1-butanol.

Gene variants encoding enzymes having 80-85% identity, 85%-90% identity, 90%-95% identity, or 95%-100% identity with amino acid sequences of the enzymes disclosed herein, in which the encoded enzymes have at least the activity of the reference enzymes, are contemplated for use in the recombinant photosynthetic microorganisms of the invention. Such gene variants may be tested for use in engineering host strains of the invention that produce one or more branched-chain alcohols using methods provided in this application or in US patent application publication 2009/0288337, incorporated by reference.

In some aspects, the invention provides a recombinant photosynthetic microorganism that includes a heterologous nucleic acid sequence that encodes a 2-ketoacid decarboxylase, in which the photosynthetic microorganism produces a branched-chain alcohol. Exemplary polypeptides catalyzing the substrate to product conversions of reactions (4), (14), and (23) include 2-oxo-acid carboxy-lyase enzymes (also referred to as alpha-ketoacid decarboxylase enzymes), including enzymes in the EC 4.1.1.1, EC 4.1.1.43, EC 4.1.1.71, EC 4.1.1.72, EC 4.1.1.74 classes, that are able to utilize branched-chain 2-oxo-carboxylic acids as substrates to produce branched-chain aldehydes. A number of genes have been identified that encode 2-oxo-acid carboxy-lyase enzymes that can be tested for activity on branched-chain 2-oxo-carboxylic acids (e.g., 2-oxo-3-methylbutanoate, 3-methyl-2-oxopentanoate, and 4-methyl-2-oxopentanoate) and introduced into photosynthetic microorganisms, including, but not limited to, the genes that encode the following enzymes (UniProtKB Accession numbers): P83779; Q6FJA3; Q12629; P33149; P28516; A2Y5L9; Q0DHF6; P51850; Q09737; P51845; P06169; Q05326; A2XFI3; Q10MW3; P51851; Q92345; P51846; Q05327; A2YQ76; Q0D3D2; Q9P7P6; O42873; P16467; P26263; Q4WXX9; Q96535; Q684K0; Q84V95; Q5BN14; Q5BN15; Q7M227; Q96536; B0ZS79; Q9SM49; B3F7U5; Q7M228; B2J634; Q1QC58; Q3EJQ4; Q8L388; Q93EN4; Q9R5L0; Q8KTX6; B0VBZ7; B0VUA9; B3Q3J2; Q5ZWD0; Q2JYJ7; Q2YVJ9; Q5FRZ6; Q4FTE7; Q2YUZ2; Q93IM7; Q2UKV4; P51844; Q0CNV1; P87208; P34734; P33287; P06672; Q0W4D3; A2Q7Q7; A3GF21; A3GGL8; O43107; Q659I2; Q8NK65; Q9UUT6; Q8NK64; A2QT68; Q4W928; A2R228; A4HQP2; A5AA75; B0DZR5; Q4WW88; O43106; Q43005; Q7U0A6; A1KI36; Q9CC97; Q73WX4; A0R2B1; A3Q3N5; A1UK81; Q1B4V6; A5U1U6; O50463; A0PVU7; A1TDK2; Q06408; A3LXV3; Q07471; Q6QBS4; Q684J7; Q9CG07; O53865; and A4F1Y5. In some embodiments, a 2-ketoacid decarboxylase enzyme encoded by a nucleic acid molecule used to engineer a photosynthetic host organism is encoded by PDC1 (protein accession number CAA97573; UniProtKB P06169) PDC5 (CAA97705; UniProtKB P16467), PDC6 (CAA39398; UniProtKB P26263), THI3 (CAA98646; UniProtKB Q07471), or ARO10 (AAB64816; UniProtKB Q06408), of *Saccharomyces cereviseae*; PDC1 (UniProtKB A3GGL8), PDC2 (UniProtKB A3GF21), PDC3 (ABN67867.1 GI:126093174; UniProtKB A3LXV3), or PDC6 (also known as PDC$_{3-6}$; ABN67867.1 GI:126093174; SEQ ID NO:8) of *Pichia stipitis*; kdcA (AAS49166; GI:44921617; UniProtKB Q6QBS4), kdcA-S286Y, kdcA-F381W, or kdcA-S286Y, F381W of *Lactococcus lactis*; Kdc of *Mycobacterium tuberculosis* (UniProtKB O53865); or indolepyruvate decarboxylase of *Salmonella enterica* (NP_461346; GI:16765731), or any genes encoding a 2-ketoacid decarboxylase or a pyruvate decarboxylase disclosed in US 2009/0288337, incorporated by reference herein. Any of these genes, variants or homologs of these genes, or others known to be or suspected of being genes that encode branched-chain 2-ketoacid decarboxylases, may be tested for use in engineering host strains of the invention that produce one or more branched-chain alcohols.

In some aspects, the invention provides a recombinant photosynthetic microorganism that includes a heterologous nucleic acid sequence that encodes an alcohol dehydrogenase, in which the photosynthetic microorganism produces a branched-chain alcohol, such as isobutanol, 3-methyl-1-butanol, or 2-methyl-1-butanol. Exemplary polypeptides catalyzing the substrate to product conversions of reactions (5), (15), and (24) include alcohol dehydrogenase enzymes (EC 1.1.1.1 and EC 1.1.1.2) that are able to utilize branched-chain aldehydes as substrates to produce the corresponding branched-chain alcohols. A number of genes have been identified as alcohol dehydrogenases that can be tested for activity on branched-chain aldehydes and introduced into photosynthetic microorganisms, including, but not limited to, the genes that encode the following enzymes (UniProtKB Accession numbers): P07327; P28469; Q5RBP7; P25405; P00325; Q5R1W2; P14139; P25406; P00327; P00326; O97959;

P00328; P80222; P30350; P49645; P06525; P41747; P12311; Q17334; P43067; P85440; P48814; Q70UN9; P23991; P19631; P23236; P48586; P09370; P22246; P07161; P12854; P08843; P26325; Q9Z2M2; Q64413; Q64415; P05336; P20369; Q07288; P00333; P00329; P80512; Q9P6C8; Q75ZX4; Q2R8Z5; P12886; P14219; P41680; P25141; O00097; Q03505; P22797; P06757; P14673; P80338; P13603; P00330; Q07264; P20368; P42327; O45687; O94038; P48815; Q70UP5; Q70UP6; P27581; P25720; P23237; P48587; P09369; P07160; P24267; P37686; P54202; Q24803; P10847; P49383; Q9P4C2; P04707; Q4R1E8; Q0ITW7; O13309; P28032; P14674; P00331; P06758; P42328; P07754; P10848; P49384; P14675; P07246; P08319; P49385; Q9QYY9; Q64563; Q09669; P80468; A6ZTT5; P10127; Q6XQ67; P38113; P28332; P41681; Q5R7Z8; Q5XI95; P40394; Q64437; P41682; O31186; Q7U1B9; P71818; P33744; P0A9Q8; P0A9Q7; P81600; P72324; Q9SK86; Q9SK87; A1L4Y2; Q8VZ49; Q0V7W6; Q8LEB2; Q9FH04; P81601; P39451; O46649; O46650; Q96533; Q3ZC42; Q17335; Q54TC2; P46415; P19854; P11766; P93629; P28474; P80360; P81431; A2XAZ3; Q0DWH1; P80572; O19053; P12711; P79896; P80467; Q9NAR7; Q00669; P21518; P25139; P48584; Q00670; P22245; Q9NG42; P28483; P48585; P51551; Q09009; P51549; P21898; Q07588; Q9NG40; Q27404; P10807; P07162; Q09010; P00334; Q00671; P25721; Q00672; P07159; P84328; P37473; P23361; P23277; Q6LCE4; Q9U8S9; Q9GN94; Q24641; P23278; Q03384; P28484; P51550; Q05114; P26719; P17648; P48977; P81786; P14940; P25988; P00332; Q2FJ31; Q2G0G1; Q2YSX0; Q5HI63; Q99W07; Q7A742; Q6GJ63; Q6 GBM4; Q8NXU1; Q5HRD6; Q8CQ56; Q4J781; P39462; P50381; Q96XE0; P51552; P32771; A7ZIA4; Q8X5J4; A7ZX04; A1A835; Q0TKS7; Q8FKG1; B1J085; P25437; B1LIP1; Q1RFI7; P44557; P39450; Q3Z550; P73138; P71017; P33010; P35630; Q24857; Q04894; P25377; O57380; P0A4X1; P0A4X0; P25984; P75214; P14941; Q3ZCJ2; 070473; P14550; Q9JII6; P50578; P51635; Q9UUN9; and P27800. In some embodiments an alcohol dehydrogenases that may be encoded by a nucleic acid molecule used to engineer a photosynthetic organism for the production of a branched-chain alcohol is encodes by ADH1 (Genbank protein accession number CAA58193), ADH2 (AAA34408;), ADH3 (CAA89229), ADH6 (CAA90836; GI:984691), ADH7 (CAA4223), GRE2 (CAA88277), SFA1 (CAA91578), or YPR1 (CAA56686) of *Saccharomyces cereviseae*; ADH3 (ABN65575), ADH6 (EAZ62840), ADH7 (CAA42237), or GRE2 (CAA88277), of *Pichia stipitis*; ADH1 (ABK75278), ADHs (AAK45115), or adhb (CAE55322) of *Mycoplasma* tuberculosis; yqhD of *E. coli* (Genbank accession YP_001745276, GI:170682079), or ADHE of *Equus caballus* (P00327), or any genes encoding alcohol dehydrogenases disclosed in US 2009/0288337, incorporated by reference herein. Any of these genes, variants or homologs of these genes, or others known to be or suspected of being genes that encode alcohol dehydrogenases, may be tested for use in engineering host strains of the invention that produce one or more branched-chain alcohols.

In some preferred embodiments, a recombinant photosynthetic microorganism includes a heterologous gene encoding a 2-ketoacid decarboxylase and a heterologous gene encoding an alcohol dehydrogenase, such as a branched-chain alcohol dehydrogenase. In some embodiments, a photosynthetic microorganism carries a heterologous gene encoding kdcA of *Lactococcus lactis* and a heterologous gene encoding adh6 of *Saccharomyces cereviseae*. In some embodiments, a photosynthetic microorganism carries a heterologous gene encoding pdc6 (also called pdc6) of *Pichia stipitis* and a heterologous gene encoding adh6 of *Saccharomyces cereviseae*. Recombinant photosynthetic microorganism that include a heterologous gene encoding a 2-ketoacid decarboxylase and a heterologous gene encoding an alcohol dehydrogenase can be used for the production of branched-chain alcohols such as one or more of isobutanol, 2-methyl-1-butanol, or 3-methyl-1-butanol.

Additional enzymatic activities that catalyze particular reactions in the overall pathway may be provided by numerous polypeptides. For example, acetolactate synthase is an example of a designation for the enzyme that catalyzes the conversion of pyruvate to 2-hydroxy-2-methyl-3-oxobutanoate. Because enzymatic nomenclature various between organisms, it should be noted that the names provided above are merely illustrative of a class of enzymes that catalyze the particular steps of the pathway. The enzymes contemplated for use with the invention are those that catalyze the reactions illustrated and are not limited to the enzymatic names provided. In addition, homologs to these genes encoding desired enzymatic activities that are identified in genomic and metagenomic sequence databases can also be tested for activity and introduced into photosynthetic microorganisms. Heterologous polypeptide-encoding sequences are linked to appropriate gene expression regulatory elements (i.e., a promoter and terminator). Altered versions of these genes and homologs that have enhanced catalytic activity (e.g., lower substrate $K_m$, reduced allosteric feedback inhibition, etc.) can also be generated by random or directed mutagenesis, and then introduced into photosynthetic microorganisms.

Exemplary polypeptides catalyzing the substrate to product conversions of reactions (1), (11), and (16) include acetolactate synthases (EC 2.2.1.6). A number of genes have been identified that encode acetolactate synthase enzymes that can be tested for appropriate activity and introduced into photosynthetic microorganisms, including, but not limited to, the genes that encode the following enzymes (UniProtKB Accession numbers): P27818, Q41768, Q6K2E8, P09342, P14874, Q41769, Q7XKQ8, P09114, P27819, P17597, P37251, P42463, Q5 KPJ5, Q6SSJ3, O19929, P08142, Q09129, O78518, P27696, Q04524, Q02137, O08353, Q57725, Q59498, P0A623, O33112, P0A622, P69683, P69684, Q1XDF6, P36620, P27868, Q7U5G1, P07342, P00892, P66947, P66946, O67703, O28555, P37252, P57320, O85294, Q89AP8, Q9TLY1, P00894, Q9MS98, O78451, P45260, Q02140, Q57625, O27492, Q59499, P65162, O33113, P65161, P51230, Q1XDQ7, P21622, Q55141, P57321, O85293, Q89AP7, Q9RQ65, P00893, P45261, P40811, P0ADG2, P0ADG1, P0ADG3, P0ADG0, P0ADF9, P0ADF8, and Q04789.

Exemplary polypeptides catalyzing the substrate to product conversions of reactions (2), (12), and (17) include ketolacid reductoisomerases (EC 1.1.1.86). A number of genes have been identified that encode ketol-acid reductoisomerase enzymes that can be tested for appropriate activity and introduced into photosynthetic microorganisms, including, but not limited to, the genes that encode the following enzymes (UniProtKB Accession numbers): Q05758, P38674, O82043, P84534, P78827, Q01292, P06168, Q81T69, Q73BA1, Q81G13, Q63DX9, Q6HLF4, Q8G6V2, Q9Z565, Q9UWX9, Q81S27, Q73A47, Q81F27, Q63CV4, Q6HKA1, Q8G6V1, Q9FBT8, Q97YJ9, Q97X13, B0CE35, A1TRT6, Q6F821, Q1ILZ3, A5G1L8, A1W6T4, A3N3E9, A6VLU1, A0KEM1, A4STE2, Q8UDV0, Q0VSB5, Q0AB89, A6TTL2, Q2IJB7, Q8YUM5, Q3MGX7, O67289, A8ERD8, O28294, A0JXZ6, A8I679, A1KAB7, Q5NXP4, A7Z7B9, A7GMU0, Q9K8E7, Q65GI7, A8FFW6, Q5WEN2, P37253, A1UT97, Q6G2T6, Q6FZ98, A91W67, Q7VRM0, Q2KWH7, Q7WCP6, Q7W566, Q7VZU4, A89G50, A5EPB5, A4YZA6, Q2YQN2, Q57CC7, A9M637, Q8YI21, A5VRC9, B0CHG8, Q8FZU1, P57655, O51888, Q89A20, Q9RQ55, Q9RQ47, Q9AQ96, Q9RQ51, Q9AQ97, Q9AQ98, Q9AQA0, Q9AQ99, Q1BUZ9, A0K937, Q0BDB6, A3MI87, A2S472, Q62IM0, A1V2K2, A3NT91, Q3JUC2, A3N7K4, Q63VP6, Q39ED2, Q2SZP8, A4JGE3, Q142I6, A4XIL7, A7ZEF1, A7GXQ8, A0RQ02, A7I0D4, A8FL53, A7H4H9, Q9PHN5, A1VYZ2, Q5HVD9, Q3AEQ7, Q9A6H4, B0T4Y1, A9WC26, Q3APC3, A1BES5, Q8KER7, Q1R092, Q7P0H9, A8ACS4, A5CPY6, B0RIN6, Q97MV0, A6LPX8, Q18C83, A0Q0E9, A9KQ65, A3DIE1, Q6NHN2, Q8FPX1, A4QDN4, Q57179, Q4JUN9, Q47BH8, Q3Z891, A5FR44, Q3ZXI2, Q1J0T2, Q9RU74, Q30ZD3, Q24XT5, A4J179, Q72CA6, A1VE41, A8LS39, A7ZTX6, P58256, A8A6N0, A1AHU6, Q0TAU6, Q8FBR2, B1IWC4, P05793, Q1R4G3, A4WG34, A7MQH1, Q6CZD1, Q2NAU8, Q0RDI8, Q2J6V2, Q5 KWJ2, Q39W76, Q74BW9, A4IRH9, A5G7V3, Q7NH80, A9GZJ4, Q5FRY8, Q0BS26, Q4QMN4, A5UE34, A5UHH1, P44822, Q0I511, B0UWE8, Q2S9V9, A1WUW3, Q5V520, Q18GT4, Q17X66, Q7VGW6, Q1CUH1, Q9ZMA9, O25097, A4G4H8, Q0C516, A6SZZ1, Q28T07, A6W7N6, A6TGG1, Q02138, A2RKQ6, Q02YY8, Q6AEP2, Q04P56, Q056H8, Q72M00, Q8EYH2, P97115, Q03UU4, Q92A29, Q71Y36, Q8Y5S0, A0AK91, Q2W1G2, A0L626, Q65WK8, A1TZ11, Q11I83, Q8TJJ4, A7I518, Q46FY8, Q12Y03, Q605K9, Q1GZE9, Q2FM37, Q58938, Q8TX44, A2SR20, A4FYE4, A6VJW0, Q8PZ26, A3CXJ5, Q6LZH4, A2SHM0, A5UMJ9, Q2NI95, O27491, A0B5E0, A6USF9, B0JRP2, Q2RIS6, A0QJC6, Q59500, P65150, A1KMZ6, A4TE07, O33114, Q73VH7, A0QUX8, A3PXP9, A1UE95, Q1BAR7, A5U713, P65149, A0PPY3, A1T6Y9, Q3IRQ2, Q5F7E5, A9M177, Q9JTI3, Q9JYI2, A1KUZ8, Q0AGM0, Q82UZ3, Q1QJU8, Q2YBU1, Q3J875, A6Q461, Q3SQ46, Q5YRW2, Q2G623, Q8EN66, A6WZX5, A1B2W3, A7HVZ2, Q9CLF1, Q3B594, A1AS39, Q4FPQ6, A9BGP6, Q7MYK9, Q6LVZ5, A1VN04, Q12B50, A4SXR3, Q9F7L6, Q6A7Z2, A3PEE9, A2C482, A8G6C6, A2CB87, A2BY22, Q319H3, Q7VAR8, Q7V8M5, Q7V0F0, A2BSN6, Q46JF6, A4SFC5, Q48N66, A6VCE7, Q02FX9, Q9HVA2, Q1I4R5, Q4K608, A4XR11, A5W952, Q3K6T1, B0KHU2, Q88DZ0, Q888N4, Q4ZY66, A4VPI6, Q4FUB6, Q1QDE6, A5WD25, Q9UZ09, Q8ZTE1, A4WLK6, A3MX05, Q8U2A3, A1RRZ8, Q0KCU2, Q473V5, Q1LPX7, Q8XXN8, A9WP08, Q2K6M2, Q1MED4, Q98KM7, Q52955, Q7UKY0, Q21T70, O32414, Q2IUS3, Q07PJ7, Q6N869, Q211Z6, Q139A2, Q2RX71, A3PH14, Q3J5C0, A4WQ93, Q0S2H3, A7NJH8, Q168N1, Q1ARE4, A1AW99, Q21HN0, A4FMQ5, A8M5F9, A9MJN4, Q57HU2, Q5PJZ5, A9MXE7, Q2S0M9, Q8Z381, A4X4A5, P05989, A8GL54, Q8E9D5, Q31UL0, Q329V3, Q7UB34, Q3YVJ0, Q5LTP7, Q1GE81, A6UAW6, Q2NQA9, Q02CM4, A9GW78, Q1GT37, A5V3W3, A7X4M9, A6U3E1, Q2FF68, Q2FWK4, A5IUK2, Q2YUF3, Q5HEE5, A6QIQ2, P65151, P65152, Q6GF17, Q6G7Q2, A8Z4V9, P65153, Q5HMG0, Q8CRQ6, Q4L7T9, Q49Z11, Q59818, A8AVN4, Q8DW43, Q04M32, Q97SD7, Q8DR03, A4W3V8, A3CQ86, A4VXL3, Q5LXV0, Q5M2F2, Q03IJ9, Q9F0I7, Q4J8K9, Q30T61, Q971A9, Q31MY7, Q8DGR0, Q2JXL2, Q2JKN5, Q5N667, A5GMM6, Q7U5Q1, A5GRI8, Q0IC80, Q3AVC2, Q3ALC5, Q0AV19, Q47SB6, Q9WZ20, A5IJM5, Q72JC8, Q5SJ03, Q8RDK4, Q31HZ1, Q3SHE4, Q8KTR6, Q10WP7, Q83HI9, Q83GP6, Q0W834, A5CWZ1, A5F449, Q9 KVI4, Q5E1S3, Q87TN4, Q8DDC8, Q7MQH3, Q7M851, Q8PH09, Q3BPK3, Q4UYF7, Q8P5L5, Q2P757, Q5H4C1, Q9PCF9, Q87CM2, A1JI57, A7FD32, Q1CBS1, Q8ZAC2, Q1CNM0, A4TRD9, Q66G37, and Q9X5F8.

Exemplary polypeptides catalyzing the substrate to product conversions of reactions (3), (13), and (18) include dihydroxy-acid dehydratases (EC 4.2.1.9). A number of genes have been identified that encode dihydroxy-acid dehydratase enzymes that can be tested for appropriate activity and introduced into photosynthetic microorganisms, including, but not limited to, the genes that encode the following enzymes (UniProtKB Accession numbers): Q10318, P39522, Q6FCR9, Q5P8J4, Q7WQA2, Q7WC98, Q7W069, Q89LK8, Q394V3, Q8FPX6, Q8TPV2, Q5Z0M2, Q3IJH1, Q475B2, Q98BZ8, Q49Z08, Q6F6Q0, Q5P6F1, Q7WJP7, Q7W497, Q7VUN6, Q89KY5, Q39DS9, Q8FMR1, Q8TKM8, Q5YX61, Q3ID04, Q46YI9, Q98LB3, Q49UX2, Q5NY71, Q7WFQ5, Q89HA2, Q5YRV8, B0CEN4, A1TMA7, Q1ILZ0, A0LSR8, A5FXD0, A3MYG9, A6VLE6, A0KQS4, Q9YG88, A4SHE9, Q8UE43, Q2IH17, A7HIA1, Q8YTE6, O67009, A8EWJ4, O29248, A0JXZ9, A8IES7, A1K344, A7Z5T7, A0RCL3, Q81S26, Q9XBI3, A7GNQ7, Q81F26, Q63CV3, Q5L918, Q64PS6, Q9K8E4, Q6HKA0, Q65IB0, A8FEC5, Q5WEM9, P51785, Q8A608, Q6G543, A9ILS3, A1A0T7, Q8G3H2, Q7VRL8, Q491Z0, Q2KZT7, Q2YNW9, Q57FS2, A9M6V2, Q8YEN0, A5VN43, B0CIL1, Q8G353, P57656, O51887, P59426, Q056W3, Q9RQ56, Q9RQ48, Q9RQ52, A3MLQ5, A2SAC7, Q62LG7, A1V5Z0, A3NSI6, Q3JV12, A3N6U9, Q63WB9, Q2T0B6, A4JN03, A4XHR9, A7GVT2, A0RRN7, A7I439, A8FJH6, A7H1A6, Q9PJ98, A1VX91, Q5HXE4, Q3AER0, P55186, A9WF68, Q3APB9, A1BES8, Q8KER4, Q1QU47, Q7NYJ7, A5CPY3, B0RIN3, Q97EE3, A6LTK6, A5N8V4, A0Q0E8, P31959, A9KT71, A3DIY3, Q47UN7, Q6NHN6, A4QDM9, Q8NQZ9, Q4JUN3, Q11NN5, Q47JC0, Q3Z888, A5FR35, Q3ZXH9, Q1IYZ8, Q9RV97, Q317H9, Q725Q1, A1V9E1, A8LKN5, A7ZTX3, Q8XAV1, A8A6M7, A1AHU3, Q0TAU9, Q8FBR5, B1IWX5, P05791, Q1R4G6, A4WG37, Q6CZC7, B0TZC0, Q2J4D1, A0Q6R5, Q5NH32, Q5KYA5, Q39W79, Q74BW7, A5G7V6, Q7NGK1, Q5FN26, Q0BQR6, Q4QMF8, A5UDY7, A5UHP2, P44851, Q0I1F1, B0UW18, Q2SA20, A1WTG1, Q5V545, Q7VHW3, A4G341, Q0C2B5, A8AB39, A6SVP5, A6TGF8, Q02139, Q02YY5, Q6AEN9, Q04RA5, Q053H5, Q72TC0, Q8F219, Q03UL2, Q92A32, Q71Y38, Q8Y5S2, A0AK88, Q2W485, A0L8Q3, Q65QD4, A6W1Q9, A6UUU2, A7I7L0, Q46AU2, Q12TW7, Q606D6, Q1H4H6, Q2FMZ1, Q58672, Q8TW40, A4FZM0, A6VIV7, Q8Q078, A3CU68, Q6M0F3, A2SFL0, A5UML4, A4YEN4, Q2NE10, O27498, A0B6Y9, A6URV4, B0JJP7, Q2RG93, A0QMH2, P65155, O06069, Q73TT7, A3PSS2, P65154, A0PMV4, Q3IMV2, Q5F8G6, Q9JUE0, Q9JS61, A1KU04, Q0ADX6, Q82XY7, Q1QRS7, Q2YC67, Q3J9N3, A6Q182, Q3SW60, A1SM84, Q2G7E9, Q8EN63, A6WV39, A6LDP0, A1B673, A7HXI4, P57957, Q3A3A5, Q3B589, A1AS43, Q4FM19, Q7MYJ5, Q6LLH7, Q6KZ30, A1VR98, Q12BW0, A3PCI2, A8G4F2, A2CAC6, A2BW57, Q31BA3, Q7VC95, Q7TV16, Q7V1T1, A2BQQ9, Q46LF6, A4SFC2, Q48PA6, Q15MY9, A6UYF6, Q02U62, Q9I6E0, Q1IGF7, Q4K498, A4Y036, A5WAG2, Q3K559, B0KN82, Q88CQ2, Q87V83, Q4ZZ83, A4VRN4, Q4FS54, A1SRU7, Q9UZ03, Q8ZYU6, A4WN46, A3MUK8, Q8U297, A1RSI5, Q8XWR1, A9WP05, Q2K917, Q1MIB2, Q92M28, Q7UJ69, P31874, Q21X56, Q2ISQ1, Q07IE7, Q6N9S5, Q2RTF9, A3PRB5, Q3IXP4, A7NNA3, A5UY13, A1AWH6, Q21NV7, A8M5F5, Q57HU7, Q5PK00, A9MXE2, Q8Z377, P40810, A1SAS5, A3D9T2, A6WTI9, A9L621, Q121N9, Q088M9, B0TJR3, A3Q9L6, Q8E9D9, A8GZD9, A4YBI7, A0KS32, A8G0Z3, Q0HNC3, Q0HQG3, A1RPG2, Q31UL3, Q329V0, Q0SYW3, Q83PI6, Q3YVJ3, Q5LN98, Q1GDP8, A6UD23, Q2NQA6, Q1GTW7, A7X4M5, A6U3D8, Q2FF71, Q2FWK7, A5IUJ9, Q2YUF6, Q5HEE8, A6QIQ0, P65156, P65157, Q6GF19, Q6G7Q4, A8Z4V6, P65158, Q5HMG3, Q8CNL6, Q4L7T6, Q82E99, O69198, Q8DRT7, Q04I44, P65159, P65160, A4W3W3, A3CR42, A4VXL9, Q5LYH1, Q5M334, Q4J860, Q30UI5, A6QD02, Q97UB2, Q96YK0, Q67KX6, Q2LXP6, Q31QL1, Q8DK13, A0LF54, Q2JTX6, Q2JK60, Q5N3N2, Q7U763, A5GTE2, Q3AXL0, Q3AK67, P74689, Q47MS7, Q9WZ21, A5IJM4, Q72JA8, Q5SIY0, Q8RDJ9, Q31I28, Q8KTS9, Q11AD1, Q83HI6, Q83GP9, A1WMU5, A5F497, Q9 KVW0, Q5E1P2, Q87 KB6, Q8DDG1, Q7MGI8, Q7MAN4, Q8PQI0, Q3BYS5, Q4UZT2, Q8PDJ3, Q2NY76, Q5GUY8, Q9PH47, Q87F63, A1JI53, A7FD26, Q1CBS9, Q8ZAB3, Q1CNM8, A4TRE8, Q66G45, and Q5NLJ4.

Exemplary polypeptides catalyzing the substrate to product conversions of reaction (6) include citramalate synthases (EC 2.3.1.182). A number of genes have been identified that encode citramalate synthase enzymes that can be tested for appropriate activity and introduced into photosynthetic microorganisms, including, but not limited to, the genes that encode the following enzymes (UniProtKB Accession numbers): Q8TJJ1, Q58787, Q8TYB1, P58966, and O26819.

Exemplary polypeptides catalyzing the substrate to product conversions of reaction (7) include 2-methylmalate dehydratases (EC 4.2.1.35). A number of genes have been identified that encode 2-methylmalate dehydratase enzymes that can be tested for appropriate activity and introduced into photosynthetic microorganisms, including, but not limited to, the genes that encode the following enzymes (UniProtKB Accession numbers): P81291 and Q58673.

Exemplary polypeptides catalyzing the substrate to product conversions of reactions (8), (20), and (21) include 3-isopropylmalate dehydratases (EC 4.2.1.33). A number of genes have been identified that encode 3-isopropylmalate dehydratase enzymes that can be tested for appropriate activity and introduced into photosynthetic microorganisms, including, but not limited to, the genes that encode the following enzymes (UniProtKB Accession numbers): O28316, Q89X98, Q9RTY9, Q65VS0, Q8TLF1, Q8TVF2, Q8PZT3, O27439, Q9UZ07, Q8U2A1, Q1AZC4, Q57TE8, P15717, Q9WYC7, O28084, Q89x34, Q9RTI6, Q65V07, Q8TQZ3, Q8TW29, Q8PUG1, O27668, Q9V1J0, Q8U0C0, Q1AVC5, Q57SN1, Q8ZRJ0, Q9WZ24, B0CG35, A1TLH6, Q6FEW0, Q1IMI3, A3M1S8, A0LVA3, A5G0G6, A1WAS7, A3MYL1, A6VQL0, Q44427, A0KGM7, A4SR64, Q8UBY9, Q0VPI0, Q0A9B0, Q2IJC2, A7HBI2, Q8YX02, Q3M614, O67078, A8EQZ0, A1R7K0, A0JXX8, Q74ZM9, A1K4A1, Q5P1J8, P96195, A7Z7B6, A0RBL4, Q81T66, Q73B98, A7GMU3, Q81G10, Q63DX6, Q5LAB1, Q64QP1, Q9K8F0, Q6HLF1, Q65GJ0, A8FFW3, Q5WEN5, P80858, Q8A6L7, A6L1V8, A0ZZS7, Q8G4W2, Q7VQJ8, Q493R2, Q7WKH6, Q7W931, Q7VY75, Q2YLP7, Q57AZ0, A9M8P2, Q8YJC9, A5VSN3, B0CIF7, Q8FYG9, P56934, O85065, P59519, Q5WPZ8, O85072, Q9EVG2, P58945, P48573, O31293, Q9EVG5, Q9EVE0, Q9EVH4, Q9EVH7, Q9AQC6, Q9EVG8, Q9EVI6, Q9EVI0, Q9EVI3, Q1BM55, A0AZ60, Q0BAC8, A3 MBT5, A2S127, Q62AI6, A1UZ32, A3P7N9, Q3JKG6, A3NM77, Q63JK9, Q393X2, Q2T7H8, A4JMB6, A8MDY8, A4XJ48, A7ZFP0, A7H0L8, A0RMG7, A7 HZP6, A8FP33, A7H665, Q9PLW1, A1W1X0, Q5HS78, Q00464, Q9ABN0, Q7NUB6, A8ALM7, Q97EE0, A6LPX4, Q18AJ2, A5MZ75, A9KT79, A3DHI4, Q47WG2, Q6NHL0, Q8FPR3, A4QDS8, P58946, Q4JUX2, Q11NN8, Q47HR4, Q30WD3, Q24XT4, Q726X4, A1VAE7, A8LKJ1, A7ZHG4, Q8XA00, A7ZW23, A1A7C0, Q0TLR7, P0A6A7, B1IRA6, P0A6A6, Q1RGC5, A4W6H7, A7MIC7, Q6D0G6, A5FKC6, Q0RDK7, Q2J6W9, Q5KWJ5, Q39W70, Q74BX5, A4IRH6, A5G7U4, Q7NFV7, Q5FUG3, Q0BRH4, Q4QLS2, A5UD83, P44968, Q0I2G3, B0USF4, Q2SJD8, A1WY14, Q5V518, Q7ZAG7, Q7VH31, A4G4F5, A6T015, Q28W60, A6T4L7, Q02142, A2RKR3, Q02YY1, Q6AFK7, Q72RC4, Q8F4E6, Q03UM2, Q92A26, Q71Y33, Q8Y5R7, A0AK94, Q2VZV4, A0L8J4, A1U0Y0, Q0AT09, A6VX34, Q11CQ6, A7IA28, Q606F2, Q1H0L4, P81291, A4YF03, B0JY97, Q2RG98, A0QJB7, Q7TXH6, A1KMY2, A4TE23, O33123, Q73V17, Q938C9, A3PXR2, A1UEA8, Q1BAQ4, A5U6Z9, O53237, A0PPZ6, A1T700, Q3IRQ4, Q5F8T1, A9LZF7, Q9JU82, Q9JZI5, A1KU80, Q82WI9, Q1QHI4, Q3J716, A6Q5L6, Q3SNV3, Q5YRY0, A1SLW5, Q2G958, Q8EN69, A6WXG4, Q04DA3, A1B513, A7HT10, Q9CJN7, Q4FP15, Q7N127, Q6LV26, P18250, Q6L0K5, A1VRR0, Q126M9, A4SWW8, A3PAX7, A2C088, A8G2R6, A2CCJ0, A2BUN7, Q31CS6, Q7VDT0, Q7V4U5, Q7V336, A2BP55, Q46HB8, Q48K99, Q15QR2, A6V2V3, Q02PT4, Q9 HZA3, Q1ICW0, Q4KF08, Q3IJS4, A4XVW2, B0KF81, Q88LE8, Q884C2, Q4ZUZ6, A4VKE7, Q4FRU7, Q1QAF2, A5WGT5, Q8ZW41, A4WMI6, A3MWJ4, O59391, A1RVH3, Q5JFV6, Q46YV7, Q44023, Q8XXX3, Q2K376, Q8VMA6, Q1MAJ9, Q98EF1, Q92L76, P55811, P55251, P17279, Q7UIA7, Q2J3A1, Q07UU3, Q6ND69, Q21CT4, Q13DU7, Q2RV55, A3PMQ9, Q3IZI8, A4WNV5, A7NJH2, Q16CH7, A5UUP5, A1AW36, Q21IY3, A4FMP2, A8M513, A9MQE0, Q5PDG3, Q2S0M6, Q8Z9I2, A4X4C8, O14289, A8G9Q9, A1S2E2, A3CZK7, A6WIB7, A9KY15, Q07WH1, B0TQM2, A3QIN8, Q8E9N4, A8H999, A4Y2M2, A0L1Q8, A8FQ85, Q0HE67, Q0HZT2, A1REY2, Q326G3, Q32K22, Q0T8C6, Q821C2, Q3Z5T8, Q5LX06, Q1GDM6, A6UE05, Q2NVW5, Q01Z81, A9GL99, Q1GR84, A7X4N3, A6U3E4, Q2FF65, Q2FWK1, A5IUK5, Q2YUF0, Q5HEE2, A6QIQ5, P63435, P63436, Q6GF14, Q6G7P9, A8Z4W2, P58947, Q5HMF7, Q8CNL1, Q4L7U2, Q49Z14, Q82JR8, O86534, A8AWP5, Q9AIM3, Q8DTG4, A3CMJ2, Q5LZF4, Q5M406, Q03 KB3, Q4JC09, Q30NZ0, A6Q6J8, Q97VY2, Q974R0, Q67MJ2, Q2LWJ2, Q31LZ1, Q8DKF0, Q2JQU3, Q2JPG2, Q5MZY3, A5GIG7, Q7U9J4, A5GWH5, Q0IDD5, Q3AW21, Q3AN00, P54384, Q47SA3, Q72JB3, Q9ZND5, Q8RDK2, Q31HI2, Q3SHL1, P49601, A5CX27, A5F5E2, Q9 KP81, Q5E858, A7MWC3, Q87SS9, Q8DED9, Q7MP79, Q7M9Z9, P58948, Q3BPJ6, Q4UYG5, P58949, Q2P765, Q5H4D1, Q9PAX0, Q87BP9, P07264, A1JJH5, A7FM86, Q1C1Z4, Q8ZIH0, Q1CMP7, A4TQA4, Q66EM3, Q5NRC5, O29626, Q7WKH5, Q7W930, Q7VYI1, Q7NW22, Q9RTY5, Q65VR9, Q8TJM9, Q8TX94, Q8PZ49, O26917, Q9UZ06, Q8U2A0, Q57TE9, P04787, Q9WYC8, O28513, Q7WIN3, Q7W749, Q7VY74, Q7NUB8, Q9RTI0, Q65V08, Q8TU71, Q8TW31, Q8PWT6, O27440, Q9V1I9, Q8U0B9, Q57SN0, Q8ZRI9, Q9WZ25, Q8TRF7, A1TLH5, Q6FEV8, Q1IMI4, A3M1S9, A0LVA2, A1WAT0, A3MYL0, A6VQL1, Q44428, A0KGM6, A4SR65, Q8UBR0, Q0VPI1, Q0A9A9, Q2IJC3, A7HBI3, Q8YX03, O67399, A8ETJ8, A1R7J9, A0JXX7, A8ILN3, A1K4A2, Q5P1J7, P96196, A7Z7B5, Q81T65, Q73B97, A7GMU4, Q81G09, Q63DX5, Q9K8F1, Q6HLF0, Q65GJ1, A8FFW2, Q5WEN6, P94568, A0ZZS8, Q8G4W1, Q7VQJ9, Q493R3, Q2KYL4, Q89X27, A5E8Z8, Q2YL51, Q579A4, A9MCG4, P65275, A9WVP8, P65276, P56935, O85066, P59516, O85073, Q9ZEZ5, P59019, P48574, O31294, Q0BAC6, A3 MBT7, A2S129, Q62AI8, A1UZ33, A3P7N7, Q3JKG8, A3NM75, Q63JL1, Q2T7H7, A4XJ49, A8FP32, A7H664, Q9PLW2, A1W1W9, Q5HS79, Q9ABN1, B0T3B7, A9WC30, Q1QUQ9, A8ALM8, A5CQN3, B0REY1, Q97EE1, Q18AJ1, P31960, Q47WG1, Q6NHK9, Q8FPR2, A4QDS9, Q8NQV7, Q4JUX3, Q11NN7, Q47HR2, Q30WD2, Q726X3, A1VAE6, A8LKI9, A7ZHG3, Q8XA01, A7ZW22, A1A7B9, Q0TLR8, Q8FL79, B1IRA7, P30126, Q1RGC6, A4W6H6, A7MQ53, Q6D0G5, Q2NC39, Q0RDK8, B0TW84, Q2J6X0, A7NES0, Q2A1A1, A0Q406, Q0BK19, Q5 KWJ6, A9HS54, Q5FUG4, Q0BRH5, A0M367, Q4QLS1, A5UD82, A5UIC6, P44438, Q0I2G4, B0USF3, Q2SJD7, Q7VH32, Q28W72, A6W7Q8, A6T4L6, Q02144, A2RKR1, Q6AFK6, Q04RN8, Q051Y3, Q72RC5, Q8F4E5, Q03UM3, Q92A25, Q71Y32, Q8Y5R6, A0AK95, Q2VZV3, A0L8J5, A1U0X9, A6VX35, Q606F3, Q8RP98, Q1H0L5, Q58673, A2SHT0, A4YF02, Q2RG99, A0QJB6, P65278, A1KMY1, A4TE22, O33124, Q73VI8, Q938C8, A3PXR3, A1UEA9, Q1BAQ3, A5U6Z8, P65277, A0PPZ7, A1T701, Q5F8T3, Q50974, P50181, A9LZF9, Q9JU81, Q9JZI6, A1KU82, Q0AGY1, Q82WI7, Q1QHH8, Q3JCC5, Q3SNU7, Q5YRY1, A1SLW4, Q2G955, Q8EN70, A6X449, Q04DA2, Q9LCR5, A1B515, A7HT11, Q9CJN8, Q4FP16, Q7N126, Q6LV27, A1VRR1, Q126M8, A4SWX0, Q48K98, A6V2V4, Q02PT3, Q9 HZA4, Q1ICV9, Q4KF07, Q3IJS5, A4XVW1, B0KF82, Q88LE7, Q884C1, Q4ZUZ5, A4VKE8, Q4FRU8, Q1QAF3, A1SVE8, A5WGT4, Q8ZW36, A3MWK3, O59393, A1RVI0, Q5JFV7, Q46YV9, Q44022, Q8XXX4, Q2K2V2, Q1MA52, Q98E51, Q92LA1, Q7UIA6, Q21XI0, Q2J3A7, Q07UT6, Q6ND74, Q21CT1, Q13DV3, Q2RV54, A3PMQ7, Q3IZJ0, A4WNV6, A7NJH1, Q16DI8, A5UUP4, Q1AZC3, A1AW35, Q21IY4, A4FMP1, A8M5I4, A9MQE1, Q5PDG4, Q8Z913, A4X4C9, A8G9Q8, A1S2E3, A3CZK8, A6WIB8, A9KY16, Q12SE4, Q07WH2, B0TQM3, A3QIN7, Q8E9N5, A8H998, A4Y2M3, A0L1Q7, A8FQ86, Q0HE68, Q0HZT1, A1REY3, Q326G4, Q32K23, Q0T8C7, P59714, Q3Z5T9, Q5LX07, Q1GDM5, A6UDX5, Q2NVW6, Q01Z80, Q1GR82, A7X4N4, A6U3E5, Q2FF64, Q2FWK0, A5IUK6, Q2YUE9, Q5HEE1, A6QIQ6, P65279, P65280, Q6GF13, Q6G7P8, A8Z4W3, Q8NVI9, Q5HMF6, Q4L7U3, Q49Z15, Q82JR9, O86535, A8AWP6, Q9AIM2, Q8DTG5, Q97QF9, A4W420, A3CMJ3, A4VXS3, Q5LZF5, Q5M407, Q03 KB4, Q4JC10, Q30RK1, A8Z5R9, Q97VY3, Q974Q9, Q67MJ3, Q2LWJ1, P74207, Q47SA2, Q72JB2, Q9ZND4, Q8RDK1, Q3SHL2, A5CX59, A5F5E3, Q9 KP80, Q5E859, A7MWB9, Q87ST0, Q8DED8, Q7MP80, Q7M887, Q8PH04, Q3BPJ7, Q4UYG4, Q8P5K9, Q2P764, Q5H4D0, Q9PAX1, Q87BQ0, A7FM87, Q1C1Z3, Q8ZIH1, Q1CMP8, A4TQA5, Q66EM4, and Q5NRC4.

Exemplary polypeptides catalyzing the substrate to product conversions of reactions (9) and (22) include 3-isopropylmalate dehydrogenases (EC 1.1.1.85). A number of genes have been identified that encode 3-isopropylmalate dehydrogenase enzymes that can be tested for appropriate activity and introduced into photosynthetic microorganisms, including, but not limited to, the genes that encode the following enzymes (UniProtKB Accession numbers): Q9SA14, Q7WNM3, Q89XA0, Q47HR1, P93832, Q7WKH4, Q89X19, Q479H7, Q9FMT1, P87256, P87257, Q6FEV6, P24404, Q2IJK7, Q8YXA2, Q3M8T9, O66607, O29627, Q8NKB8, O60027, Q5P1J6, P96197, Q81T67, Q73B99, P05644, P12010, Q81G11, Q63DX7, Q5LAB4, P54354, Q9K8E9, Q6HLF2, Q65GI9, P41019, Q5WEN4, P05645, Q8A6M0, Q8G500, Q7VQJ7, Q493R1, Q2KYL5, Q7W929, Q7VY73, P29102, Q2YL58, Q579B1, Q8YCX4, Q8FVF3, P56933, O85064, P59515, Q5WPZ9, O85071, Q9EVG3, P59027, P48572, O31292, Q9EVG6, Q9EVE1, Q9EVH5, Q9EVH8, Q9AQC8, Q9EVG9, Q9EVI7, Q9EVI1, Q9EVI4, Q845W3, Q62AI9, Q3JKG9, Q63JL2, Q393X4, Q2T7H6, Q9PLW0, Q5HS77, P87186, Q01987, O14429, P07139, Q6PY58, Q9HDQ5, Q3AEQ2, Q9ABN3, Q12545, Q3APC4, P59028, Q1QUR0, Q7NUC2, A5CPZ4, B0RIP4, Q97EE2, P31958, Q47WG3, Q6NHM7, Q8FPV5, A4QDP9, P94631, Q4JUQ0, Q6B458, Q3Z896, Q3ZXI7, Q1IZK2, Q9RTH9, Q30WD0, Q24XT2, Q6ANR1, Q726X1, Q8X9Z9, Q8FL76, P30125, Q1RGC4, Q6D0G7, Q2J6V8, Q5KWJ4, Q39Y29, Q748X2, Q7NFH4, Q5FUG5, Q4QLS3, P43860, Q2SJD6, Q9HDQ1, Q7VH33, Q28W67, P23390, P41766, Q02143, Q6AEP6, Q72RH7, P24015, Q92A27, Q71Y34, Q8Y5R8, Q2VZV2, Q65V05, Q606F4, Q58130, O27441, Q2RGA0, A0QJC2, P94929, A1KMY9, A4TE12, Q9Y897, O33117, Q73VI1, A3PXQ2, A1UE98, Q1BAR4, A5U706, P95313, A0PPY6, A1T6Z4, Q5F8T6, P50180, Q9JU79, Q9JZI9, P34738, Q82WI6, Q2Y7Q8, Q3JCC4, Q3SNU3, Q5YRX2, Q2G4X5, Q8EN68, Q9CJN6, Q3A3B2, Q3B595, Q4FP17, O59930, Q7N128, Q6LV25, P34733, P08791, O94114, Q31B91, Q7VC80, Q7V842, Q7V1R9, Q46LE2, Q48K97, Q51375, Q4KF05, Q3IJS3, Q3KF21, Q88LE5, Q884C0, Q4ZUZ4, Q4FRV0, Q1QAF5, Q46YW0, Q1LKH7, Q8XXX5, Q2K2V0, Q1MA50, Q98E57, Q92KY8, Q7UIE1, Q21XI1, Q2J3B4, Q6ND82, Q21CS1, Q2RV53, Q3IZJ3, Q0S2H1, Q21IY5, A4FMQ2, Q96WT9, Q57TE7, Q5PDG2, Q2S0M8, Q8Z9I1, P37412, P18869, Q8E9N3, Q326G2, Q32K21, Q83SP1, Q3Z5T7, Q5LWZ5, Q2NVW4, P29696, Q6TWC4, Q00412, Q2FF66, Q2FWK2, Q2YUF1, Q5HEE3, P65100, P65101, Q6GF15, Q6G7Q0, Q8NVJ0, Q5HMF8, Q8CNL2, Q4L7U1, Q49Z13, Q82JN6, O86504, Q8DTG3, Q8DPJ4, Q5LZF3, Q5M405, Q30RK2, Q9UXB2, P50455, Q67JY2, Q31N34, P59029, Q2JTN8, Q2JL30, Q5MZ4A0, Q7U840, Q3AYS1, Q3AIH4, P73960, P24098, Q47SB4, Q9WZ26, P61494, Q5SIY4, P61495, Q8RDK0, Q31HI0, Q3SHL3, Q56268, Q9 KP82, Q5E857, Q87SS8, Q8DEE0, Q7MP78, Q7M886, Q8PH05, Q3BPJ8, Q4UYG2, Q8P5L1, Q2P762, Q5H4C7, Q9PAX3, Q87BQ1, P41926, P18120, P04173, Q8ZIG9, Q66EM2, Q9P3Y0, Q96WI0, and Q5NPQ9.

Exemplary polypeptides catalyzing the substrate to product conversions of reaction (10) include threonine ammonia-lyase (EC 4.3.1.19). A number of genes have been identified that encode threonine ammonia-lyase enzymes that can be tested for appropriate activity and introduced into photosynthetic microorganisms, including, but not limited to, the genes that encode the following enzymes (UniProtKB Accession numbers): P09367, P25379, Q9ZSS6, Q9KC63, P37946, P53607, Q39469, Q04513, P04968, P46493, Q02145, P66898, Q9X7F1, P66897, Q9CKJ2, P20506, P25306, P31212, Q2FF63, Q2FWJ9, Q2YUE8, Q5HEE0, Q99SJ1, Q7A4H2, Q3V7T5, Q3V7T4, Q8NVI8, Q5HMF5, Q8CNK9, Q4L7U4, Q49Z16, P0AGF8, P0AGF7, P0AGF6, P11954, P0AGF9, Q2FH01, Q2FYJ3, Q2YY67, Q5HFY5, Q99U50, Q7A5L8, Q6GGX0, Q6G9C4, Q8NWQ4, O42615, O94634, P00927, and P55664.

Exemplary polypeptides catalyzing the substrate to product conversions of reaction (19) include 2-isopropylmalate synthases (EC 2.3.3.13). A number of genes have been identified that encode 2-isopropylmalate synthase enzymes that can be tested for appropriate activity and introduced into photosynthetic microorganisms, including, but not limited to, the genes that encode the following enzymes (UniProtKB Accession numbers): Q9LPR4, O29305, Q8TKQ6, Q57926, Q8TW28, P58967, O27667, Q9UZ08, Q8XXP1, Q97ZE0, Q974X3, Q8RDK3, Q9C550, O30020, Q8THA5, Q58595, Q8TYM1, P58968, O27525, Q9V1J1, Q8XSZ5, Q97W36, Q971S5, Q8RCF9, O04973, O04974, Q8UD63, P48575, O67862, A0JX36, Q81T68, Q9K8E8, Q8RL85, P94565, Q7VQJ6, Q89 GB0, Q8YIJ3, Q8FZC4, Q9ZEY8, O85063, Q89A49, Q5WQ01, O85070, Q9EVG4, P58898, P48571, O31287, Q9EVH6, Q9EVE3, Q9EVH0, Q9EVI8, Q9PLV9, Q9A823, Q7P0H2, Q97MC5, Q8FU05, A4QAP0, P42455, P85362, Q9RUA9, Q8X9Z8, Q8FL75, P09151, Q7NI93, P43861, Q7VH30, A6WDF2, Q02141, Q72RL9, Q8F445, Q92A28, Q71Y35, Q8Y5R9, P94907, Q7TVV6, Q9CB76, P96420, A0PVE6, Q9JUK6, Q9JZG1, Q820M0, Q8EN67, Q9CJN5, Q7N129, Q7VBG1, Q7TUV5, Q7V121, Q48LY5, A6V0X2, Q9HXK5, Q1I5K2, Q4K6V7, A4XY24, A5VZB6, Q3K7C3, B0KRD9, Q88P28, Q886Y1, Q4ZX14, A4VNV6, Q8ZW35, Q8U2A2, O59390, Q1MDH6, Q98HN3, Q9X7L2, Q7UI51, Q8Z9I0, P15875, O59736, Q8E9N2, Q83SP0, Q39891, Q5HEE4, P63476, P63477, Q6GF16, Q6G7Q1, P58899, Q5HMF9, Q8CNL3, Q4L7U0, Q49Z12, Q82BV3, O31046, Q8DJ32, Q7U892, P48576, Q9WZ23, Q56216, Q9 KP83, Q87SS7, Q8DEE1, Q7MP77, Q7M9W4, P58900, P58901, Q9PCG3, Q87CL8, P06208, Q8ZIG8, Q66EM1, and Q12166.

Host Organisms

The host cells used to prepare the cultures of the invention include cells of any photosynthetic microorganism which is able to convert inorganic carbon into a substrate that is in turn converted to branched-chain alcohols. These organisms include prokaryotes as well as eukaryotic organisms such as algae and diatoms. Carbon dioxide (which, along with carbonic acid, bicarbonate and/or carbonate define the term "inorganic carbon") is converted to a reduced carbon molecule in the photosynthetic process. An inorganic carbon source can be used to supply inorganic carbon to the photosynthetic microorganism, in which the inorganic carbon source includes any way of delivering inorganic carbon, optionally in admixture with any other combination compounds which do not serve as the primary carbon feedstock, but only are present as a mixture or carrier (for example, emissions from biofuel (e.g., ethanol) plants, power plants, refineries, as well as atmospheric sources).

Host organisms include eukaryotic microalgae and cyanobacteria (blue-green algae). Representative algae include green algae (chlorophytes), red algae, diatoms, prasinophytes, glaucophytes, chlorarachniophytes, euglenophytes, chromophytes, and dinoflagellates. A number of cyanobacterial species are known and have been manipulated using molecular biological techniques, including the unicellular cyanobacteria *Synechocystis* sp. PCC6803 and *Synechococcus elongatus* PCC7942, whose genomes have been completely sequenced.

The following genera of cyanobacteria may be used: one group includes *Chamaesiphon, Chroococcus, Cyanobacterium, Cyanobium, Dactylococcopsis, Gloeobacter, Gloeocapsa, Gloeothece, Microcystis, Prochlorococcus, Prochloron, Synechococcus,* and *Synechocystis*. Another group includes: *Chroococcidiopsis, Cyanocystis, Dermocarpella, Myxosarcina, Pleurocapsis, Stanieria,* and *Xenococcus*. Still another group includes *Arthrospira, Borzia, Crinalium, Geitlerinema, Halospirulina, Leptolyngbya, Limnothrix, Lyngbya, Microcoleus, Oscillatoria, Planktothrix, Prochlorothrix, Pseudanabaena, Spirulina, Starria, Symploca, Trichodesmium,* and *Tychonema*. Still another group includes *Anabaena, Anabaenopsis, Aphanizomenon, Calothrix, Cyanospira, Cylindrospermopsis, Cylindrospermum, Nodularia,* and *Nostoc*; and another group includes *Chlorogloeopsis, Fischerella, Geitleria, Nostochopsis, Iyengariella, Stigonema, Rivularia, Scytonema,* and *Tolypothri*.

In addition, various algae, including diatoms and green algae can be employed. Eukaryotic microalgae that can be used in the methods of the invention can include, but are not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella,* or *Volvox* species.

Transformation of Host Organisms

Photosynthetic microorganisms can be transformed by any suitable methods, including, as nonlimiting examples, natural DNA uptake (Chung et al. (1998) *FEMS Microbiol. Lett.* 164: 353-361; Frigaard et al. (2004) *Methods Mol. Biol.* 274: 325-40; Zang et al. (2007) *J. Microbiol.* 45: 241-245), conjugation, transduction, glass bead transformation (Kindle et al. (1989) J. Cell Biol. 109: 2589-601; Feng et al. (2009) *Mol. Biol. Rep:* 36: 1433-9; U.S. Pat. No. 5,661,017), silicon carbide whisker transformation (Dunahay et al. (1997) *Methods Mol. Biol.* (1997) 62: 503-9), biolistics (Dawson et al. (1997) *Curr. Microbiol.* 35: 356-62; Hallmann et al. (1997) *Proc. Natl. Acad. USA* 94: 7469-7474; Jakobiak et al. (2004) *Protist* 155:381-93; Tan et al. (2005) *J. Microbiol.* 43: 361-365; Steinbrenner et al. (2006) *Appl Environ. Microbiol.* 72: 7477-7484; Kroth (2007) *Methods Mol. Biol.* 390: 257-267; U.S. Pat. No. 5,661,017) electroporation (Kjaerulff et al. (1994) *Photosynth. Res.* 41: 277-283; Iwai et al. (2004) *Plant Cell Physiol.* 45: 171-5; Ravindran et al. (2006) *J. Microbiol. Methods* 66: 174-6; Sun et al. (2006) *Gene* 377: 140-149; Wang et al. (2007) *Appl. Microbiol. Biotechnol.* 76: 651-657; Chaurasia et al. (2008) *J. Microbiol. Methods* 73: 133-141; Ludwig et al. (2008) *Appl. Microbiol. Biotechnol.* 78: 729-35), laser-mediated transformation, or incubation with DNA in the presence of or after pre-treatment with any of poly (amidoamine) dendrimers (Pasupathy et al. (2008) *Biotechnol. J.* 3: 1078-82), polyethylene glycol (Ohnuma et al. (2008) *Plant Cell Physiol.* 49: 117-120), cationic lipids (Muradawa et al. (2008) *J. Biosci. Bioeng.* 105: 77-80), dextran, calcium phosphate, or calcium chloride (Mendez-Alvarez et al. (1994) *J. Bacteriol.* 176: 7395-7397), optionally after treatment of the cells with cell wall-degrading enzymes (Perrone et al. (1998) *Mol. Biol. Cell* 9: 3351-3365). *Agrobacterium*-mediated transformation can also be performed on algal cells, for example after removing or wounding the algal cell wall (e.g., WO 2000/62601; Kumar et al. (2004) *Plant Sci.* 166: 731-738). Biolistic methods are particularly successful for transformation of the chloroplasts of plant and eukaryotic algal species (see, for example, Ramesh et al. (2004) *Methods Mol. Biol.* 274: 355-307; Doestch et al. (2001) *Curr. Genet.* 39: 49-60; U.S. Pat. No. 7,294,506; WO 2003/091413; WO 2005/005643; and WO 2007/133558, all incorporated herein by reference in their entireties).

In some preferred embodiments of the invention, a gene encoding an enzyme that participates in a pathway that leads to the synthesis of a branched-chain alcohol (such as an enzyme disclosed herein), is cloned into an expression vector for transformation into an alga or photosynthetic bacterium. The vector includes sequences that promote expression of the transgene of interest, such as a promoter, and, where the engineered host strain is a eukaryotic microalga, may optionally include a transit peptide-encoding sequence for directing the expressed enzyme to the chloroplast of transformed eukaryotic cells, an intron sequence, a sequence having a polyadenylation signal, etc. Alternatively, if the vector does not contain a promoter in operable linkage with the gene of interest, the gene can be transformed into the cells such that it becomes operably linked to an endogenous promoter by homologous recombination or vector integration.

In some embodiments, a vector is designed for integration of the heterologous nucleic acid sequence into the host genome. For example, vectors can be: 1) targeted for integration into an algal or cyanobacterial chromosome by including flanking sequences that enable homologous recombination into the chromosome, 2) targeted for integration into endogenous host plasmids by including flanking sequences that enable homologous recombination into the endogenous plasmids, or 3) designed such that the expression vectors replicate within the chosen host.

Artificial chromosome vectors can also be used for the transformation of photosynthetic microorganisms when more than one gene that encodes an enzyme that participates in the synthesis of a branched-chain alcohol is transformed into an organism.

In some cases in which the nucleus of a eukaryotic host organism is transformed, it may be advantageous to include a sequence encoding a chloroplast transit peptide in the heterologous gene construct. The transit peptide sequence can be derived from a gene endogenous to the host organism, or can be derived from a gene from another species.

In some cases in which it may be advantageous to transform the chloroplast of a eukaryotic alga, vectors can be designed to have regions of sequences flanking the transgene (e.g., a 2-ketoacid decarboxylase gene) that are homologous to chloroplast sequences to promote homologous recombination and integration of the sequence of interest. In these embodiments, the vector preferably includes a promoter for expressing the transgene, in which the promoter functions in the chloroplast.

Vectors designed for expression of a gene in microalgae can in some embodiments include a promoter active in microalgae operably linked to the exogenous gene being introduced. A variety of gene promoters and terminators that function in green algae can be utilized in expression vectors, including, but not limited to promoters and terminators from *Chlamydomonas* and other algae (see, for example, *Plant Cell Physiol* 49: 625-632 (2008)), promoters and terminators from viruses, and synthetic promoters and terminators. Expression constructs can also optionally include an intron, such as an intron sequence from the host organism inserted into the exogenous gene, for optimal expression of the gene in the host.

For transformation of diatoms, a variety of gene promoters that function in diatoms can be utilized in these expression vectors, including, but not limited to: 1) promoters from *Thalassiosira* and other heterokont algae, promoters from viruses, and synthetic promoters. Promoters from *Thalassiosira pseudonana* that would be suitable for use in expression vectors include an alpha-tubulin promoter, a beta-tubulin promoter, and an actin promoter. Promoters from *Phaeodactylum tricornutum* that would be suitable for use in expression vectors include an alpha-tubulin promoter, a beta-tubulin promoter, and an actin promoter. The terminators associated with these genes, other diatom genes, or particular heterologous genes can be used to stop transcription and provide the appropriate signal for polyadenylation.

In some instances it can be advantageous to express a heterologous enzyme at a certain point during the growth of the transgenic host to minimize any deleterious effects on the growth of the transgenic organism and/or to maximize production of the branched-chain alcohol. In these instances one or more exogenous genes introduced into the transgenic organism can be operably linked to an inducible promoter. The promoter can be a lac promoter, a tet promoter (e.g., U.S. Pat. No. 5,851,796), a hybrid promoter that includes either or both of portions of a tet or lac promoter, a hormone-responsive promoter (e.g., an ecdysone-responsive promoter, e.g., U.S. Pat. No. 6,379,945) a metallothionien promoter (U.S. Pat. No. 6,410,828), or a pathogenesis-related (PR) promoter that can be responsive to a chemical such as, for example, salicylic acid, ethylene, thiamine, or BTH (U.S. Pat. No. 5,689,044). An inducible promoter can also be responsive to light or dark (U.S. Pat. Nos. 5,750,385, 5,639,952) or temperature (U.S. Pat. No. 5,447,858; Abe et al., *Plant Cell Physiol.* 49: 625-632 (2008); Shroda et al. *Plant J.* 21: 121-131 (2000)), or copper level (Surzycki et al. *Proc Natl Acad Sci USA.* 104: 17548-17553 (2007)). The foregoing list is exemplary and not limiting. The promoter sequences can be from any organism, provided that they are functional in the host organism. Inducible promoters as used in the constructs of the present invention can use one or more portions or one or more domains of the aforementioned promoters or other inducible promoters fused to at least a portion of a different promoter that operates in the host organism to confer inducibility on a promoter that operates in the host species.

A variety of gene promoters that function in cyanobacteria can be utilized in expression vectors, including, but not limited to: 1) the lac, tac, and trc promoters that are inducible by the addition of isopropyl β-D-1-thiogalactopyranoside (IPTG), 2) promoters that are naturally associated with transposon- or bacterial chromosome-borne antibiotic resistance genes (neomycin phosphotransferase, chloramphenicol acetyltrasferase, spectinomycin adenyltransferase, etc.), 3) promoters of various heterologous bacterial and native cyanobacterial genes, 4) promoters from viruses and phages, and 5) synthetic promoters. Promoters isolated from cyanobacteria that have been used successfully include the following:

secA (secretion; controlled by the redox state of the cell)
rbc (Rubisco operon)
psaAB—(PS I reaction center proteins; light regulated)
psbA—(D1 protein of PSII; light-inducible)
nirA—(nitrate reductase, NH3/NO3 regulated)

Likewise, a wide variety of transcriptional terminators can be used for expression vector construction. Examples of possible terminators include, but are not limited to, psbA, psaAB, rbc, secA, and T7 coat protein.

Transformation vectors preferably also include a selectable marker, such as but not limited to a drug resistance gene, an herbicide resistance gene, a metabolic enzyme or factor required for survival of the host (for example, an auxotrophic marker), etc. Transformed cells can be optionally selected based upon the ability to grow in the presence of the antibiotic or other selectable marker under conditions in which cells lacking the resistance cassette or auxotrophic marker would not grow. In some embodiments a non-selectable marker may be present on a vector, such as a gene encoding a fluorescent protein or enzyme that generates a detectable reaction product. In an alternative transformation strategy, selectable or non-selectable markers can be provided on a separate construct, where both the gene-of-interest construct and the selectable marker construct are used together in transformation protocols, and selected transformants are analyzed for co-transformation of the construct that includes the gene-of-interest (see, for example, Kindle (1990) *Proc. Natl. Acad. Sci. USA* 87: 1228-32; Jakobiak et al. (2004) Protist 155:381-93).

Methods for Producing Branched-Chain Alcohols

A further aspect of the invention is a method for producing a branched-chain alcohol in which the method includes culturing a recombinant photosynthetic microorganism as provided herein to produce a branched-chain alcohol. The photosynthetic microorganism can be, for example, a photosynthetic microorganism that carries a heterologous gene encoding at least one polypeptide that catalyzes a substrate to product conversion that leads to the synthesis of isobutanol, a heterologous gene encoding at least one polypeptide that catalyzes a substrate to product conversion that leads to the synthesis of 2-methyl-1-butanol, or a heterologous gene encoding at least one polypeptide that catalyzes a substrate to product conversion that leads to the synthesis of 3-methyl-1-butanol. In some preferred embodiments, a photosynthetic microorganism used for the production of one or more branched-chain alcohols includes a heterologous nucleic acid sequence encoding a branched-chain 2-ketoacid decarboxylase and a heterologous nucleic acid sequence encoding an alcohol dehydrogenase.

The photosynthetic microorganism can be cultured mixotropically, in which the microorganism is grown in the light for at least a portion of the growth period and is also supplied with a reduced carbon source, or can be cultured photoautrophically. In some embodiments the photosynthetic microorganism is cultured under photoautotrophic conditions, in which the culture lacks a reduced carbon source and the organism is supplied with or exposed to light for at least a portion of the time it is in culture. The photoautotrophic culture is in some embodiments provided with inorganic carbon such as $CO_2$, carbonic acid, or a carbonate salt. An inorganic carbon source such as flue gas or air can also be provided.

In preferred embodiments, the methods for producing a branched-chain alcohol include culturing a photosynthetic microorganism photoautotrophically using inorganic carbon as the sole source of carbon for incorporation into biomass or algal products. In these embodiments, the culture medium for photoautotrophic growth lacks sugars, organic acids, or other forms of reduced carbon that can be used as an energy source, although it may contain one or more reduced carbon molecules in amounts that are insufficient for supplying the culture with a source of energy for supporting cell division and/or biomass accumulation (for example, a vitamin such as thiamine).

A photosynthetic microorganism used in the methods that includes a heterologous nucleic acid sequence encoding a branched-chain 2-ketoacid decarboxylase and a heterologous nucleic acid sequence encoding an alcohol dehydrogenase may further include at least one heterologous nucleic acid sequence encoding one or more of an acetolactate synthase (EC 2.2.1.6), a ketol-acid reductoisomerase (EC 1.1.1.86), or dihydroxyacid dehydratase EC 4.2.1.9. The culture is in some preferred embodiments produces isobutanol, 2-methyl-1-butanol, or 3-methyl-1-butanol, or a combination thereof.

In some embodiments, the photosynthetic-microorganism produces 3-methyl-1-butanol. In some embodiments, the photosynthetic microorganism produces 3-methyl-1-butanol and is engineered to include at least one heterologous nucleic acid sequence encoding one or more of the enzymes 2-isopropylmalate synthase (EC 2.3.3.13), 3-isopropylmalate dehydratase (EC 4.2.1.33), or 3-isopropylmalate dehydrogenase (EC 1.1.1.85) in addition to a heterologous nucleic acid sequence encoding a branched-chain 2-ketoacid decarboxylase and a heterologous nucleic acid sequence encoding an alcohol dehydrogenase.

In some embodiments, the photosynthetic microorganism produces 2-methyl-1-butanol. In some embodiments, the photosynthetic microorganism produces 2-methyl-1-butanol and is engineered to include at least one nucleic acid sequence encoding one or more of the enzymes homoserine dehydrogenase (EC 1.1.1.3), homoserine kinase (EC 2.7.1.39), threonine synthase (EC 4.2.3.1), or threonine ammonia-lyase (EC 4.3.1.19) in addition to a heterologous nucleic acid sequence encoding a branched-chain 2-ketoacid decarboxylase and a heterologous nucleic acid sequence encoding an alcohol dehydrogenase.

In some embodiments, the method includes recovering the branched-chain alcohol from the culture medium, for example, using methods such as liquid-liquid extraction, gas stripping, steam stripping, or pervaporation (Qureshi et al. *Biotechnol Prog.* 15:594-602 (1999), Jitesh et al. *Bioseparation* 9:145-154 (2000), Ezeji et al. *Bioprocess Biosyst Eng.* 27: 207-214 (2005), Qureshi et al. *Bioprocess Biosyst Eng.* 27: 215-222 (2005), Ezeji et al. *J Ind Microbiol Biotechnol* 34: 771-777 (2007), Izak et al. *Appl Microbiol Biotechnol.* 78: 597-602 (2008), Zeng et al. *J Ind Microbiol Biotechnol* 36: 1127-1138 (2009). Any of these methods may be used in combination with distillation. The methods can in some embodiments be used for extraction of products from a continuous culture.

In a further aspect, included within the scope of the invention is a branched-chain alcohol made by the methods provided herein. The branched-chain alcohol produced by a recombinant photosynthetic microorganism can be, for example, isobutanol, 2-methyl-1-butanol, or 3-methyl-1-butanol. Also included are compositions that include a branched-chain alcohol produced by a recombinant photosynthetic organism as disclosed herein. The composition can be, for example, a fuel or solvent.

In another embodiment of this invention, the branched-chain alcohols can be chemically dehydrated to the corresponding alpha-olefins. For example, isobutanol can be used to produce 2-methylpropene (isobutylene) or isooctane, 2-MBO can be used to produce 2-methyl-1-butene, and 3-MBO can be used to produce 3-methyl-1-butene. Such compounds have uses that are known in the art, for example, in the petroleum industry. Such compounds can be further used to produce other compounds, for example, both 2-methyl-1-butene and 3-methyl-1-butene can be used to produce 3,3,5-trimethylpentane. All of the branched-chain alcohols can also be used to produce their corresponding ethers. The esters from certain compounds, such as 2-MBO or 3-MBO, can be used as flavors or fragrances.

The following examples are offered to illustrate but not to limit the invention.

Example 1

Production of Isobutanol, 2-Methyl-1-Butanol, and 3-Methyl-1-Butanol in the Cyanobacterium *Synechococcus*

A DNA fragment comprising a functional operon was synthesized such that it contained the following elements in the given order: 1) the trc promoter, the *Saccharomyces cerevisiae* pyruvate decarboxylase gene (PDC1, GenBank Accession No. X77316) codon-optimized for expression in *Synechococcus elongatus* PCC 7942, the *S. elongatus* KaiBC intergenic region, the *S. cerevisiae* alcohol dehydrogenase gene (ADH2, GenBank Accession No. J01314) also codon-optimized for expression in *S. elongatus*, and the rrnB terminator. The nucleotide sequence of this functional operon is provided in SEQ ID NO:1 (FIG. 3). Codon optimization was performed by the use of the "Gene Designer" (version 1.1.4.1) software program provided by DNA2.0, Inc. The plasmid pSGI-BL3 was constructed by inserting the operon between SpeI and SacI restriction site in the vector pAM2314 (Mackey et al., Methods Mol. Biol. 362:115-29), which enables transformation of S. elongatus via integration into the "NS1" site of the S. elongatus PCC 7942 chromosome.

An additional vector was constructed to enable the expression and testing of a different 2-ketoacid decarboxylase gene, the Lactococcus lactis KDCa gene (GenBank Accession No. AY548760), in combination with the codon-modified S. cerevisiae ADH2 gene. The nucleotide sequence of this KDCa/ADH2 functional operon is provided in SEQ ID NO:2 (FIG. 4). This operon was placed between the SpeI and SacI restriction sites in the plasmid pAM2314 to form pSGI-BL19.

An additional vector was constructed to enable the expression and testing of a different alcohol dehydrogenase gene (the S. cerevisiae ADH6 gene with gene ID number 855368, encoding the protein provided as Genbank accession number NP_014051.1 GI:6323980) in combination with the codon-optimized S. cerevisiae PDC 1 gene. The nucleotide sequence of this PDC1/ADH6 functional operon is provided in SEQ ID NO:3 (FIG. 5). This operon was placed between the SpeI and SacI restriction sites in the plasmid pAM2314 to form pSGI-BL20.

An additional vector was constructed to enable the expression and testing of the L. lactis KDCa gene in combination with the S. cerevisiae ADH6 gene. The nucleotide sequence of this KDCa/ADH6 functional operon is provided in SEQ ID NO:4 (FIG. 6). This operon was placed between the SpeI and SacI restriction sites in the plasmid pAM2314 to form pSGI-BL21.

Synechococcus elongatus PCC 7942 cells were transformed with plasmids pSGI-BL3, pSGI-BL19, pSGI-BL20, and pSGI-BL21 as described by Golden and Sherman (J. Bacteriol. 158:36-42). Both recombinant and wild-type control strains were pre-cultivated in 20 mL of BG-11 medium to mid-log phase (OD730 nm=0.7-0.9) on a rotary shaker (150 rpm) at 30° C. with constant illumination (30 µEinsteins m-2 sec-1).

BG-11 medium was made by combining in a total volume of one liter: 10 ml of '100×BG-11'; 1 ml of 6 mg/ml Ferric ammonium citrate; 1 ml of 2% $Na_2CO_3$; and 1 ml of 3.05% $K_2HPO_4$. The components of '100×BG-11' were 149.60 g of $NaNO_3$, 7.49 g $MgSO_4.7H_2O$, 3.60 g $CaCl_2.2H_2O$, 0.60 g citric acid (or 0.89 g Na-citrate, dehydrate); 1.12 ml 0.25M $Na_2EDTA$, pH 8.0; and 100 ml Trace minerals in a final volume of one liter. (Trace minerals solution included: 2:86 g/L $H_3BO_3$, 1.81 g/L $MnCl_2.4H_2O$; 0.222 g/L $ZnSO_4.7H_2O$; 0.39 g/L $Na_2MoO_4.2H_2O$; 0.079 g/L $CuSO_4.5H_2O$; and 0.0494 g/L $Co(NO_3)_2.6H_2O$ per liter.)

Mid-log phase cultures were inoculated in BG-11 containing 1 mM IPTG to obtain 40 mL of culture having an initial culture OD730 nm of 0.3-0.4). Cultivation was performed under the same conditions as pre-cultivation. Spectinomycin (5 µg/ml) was included in recombinant cultures as appropriate. Four mL of culture were collected every 48 hours and centrifuged at 6,000 g for 10 min. Culture supernatants were transferred into clean 1.5 mL microfuge tubes for gas chromatographic analysis.

2-methyl-1-butanol and 3-methyl-1-butanol were separated from the culture supernatant by liquid-liquid extraction, using 1 volume of culture supernatant to 2 volumes of $CH_2Cl_2$, for gas chromatography-mass spectrometry analysis. A 1 uL sample was injected at a 20:1 split ratio onto an Rtx-624 column (Restek, 20 m×180 µm×1 µm), which was equilibrated for 0.5 min and then operated using the following temperature gradient: 70° C. for 1 min, 10° C./min to 110° C. for 0.5 min and then 20° C./min to 140° C. for 0.5 min, 7.5 min run time at 140° C., and 2 min post run time at 200° C. (0.75 mL/min He).

For isobutanol analysis, the culture supernatant was passed through 0.2 m PVDF filter and then analyzed directly by gas chromatography using flame ionization detection. An HP-Innowax column (Agilent, 15 m×250 µm×0.25 µm) was equilibrated for 0.5 min and then operated using the following temperature gradient: 35° C. for 2 min, 25° C./min to 180° C. for 0.2 min, 8 min run time and 2 min post run time at 220° C. (0.75 ml/min He). A 1 uL sample was injected at a 40:1 split ratio with a 250° C. injection port temperature.

Results indicating the levels of 2-methyl-1-butanol, 3-methyl-1-butanol, and isobutanol in Synechococcus elongatus PCC 7942 cultures 96 hours after culture inoculation and induction are shown in Table 1.

TABLE 1

Branched-Chain Alcohol Production (in µM) in Synechococcus elongates PCC 7942

|  | Wild-type PCC 7942 | pSGI-BL3 (PDCI/ADH2) | pSGI-BL19 (KDCa/ADH2) | pSGI-BL20 (PDCI/ADH6) | pSGI-BL21 (KDCa/ADH6) |
|---|---|---|---|---|---|
| 2-Methyl-1-Butanol | ND | ND | ND | ND | 31 |
| 3-Methyl-1-Butanol | ND | ND | 6.5 | ND | 103 |
| Isobutanol | ND | ND | 18 | ND | 394 |

Note:
ND represents "not detected" (<5uM).
2-Methyl-1-Butanol and 3-Methyl-1-Butanol were identified and quantified by GC-MS.
Isobutanol was identified and quantified by GC-FID.

Example 2

Production of Isobutanol, 2-Methyl-1-Butanol, and 3-Methyl-1-Butanol in the Cyanobacterium Synechocystis The functional operon (expression cassette) containing the codon-modified S. cerevisiae PDC1 and ADH2 genes as represented in SEQ ID NO: 1 was digested by restriction enzymes Bgl II and SacI and inserted into plasmid pSGI-YC3 between the restriction sites BamHI and SacI to form plasmid pSGI-BL7, which enables integration of the functional operon into the Synechococcus sp. PCC 6803 chromosome at the "RS1" recombination site (Williams, Methods Enzymol. 167:766-778). Plasmid pSGI-BL22 contains the S. cerevisiae codon-modified PDC1 and native ADH6 genes as represented in SEQ ID NO:3 and was made by inserting a SpeI/SacI fragment from plasmid pSGI-BL20 into SpeI/SacI-digested pSGI-YC3. Plasmid pSGI-BL23 contains the L. lactis KDCa and S. cerevisiae native ADH6 genes as represented in SEQ ID NO:4 and was made by inserting a SpeI/SacI fragment from plasmid pSGI-BL21 into SpeI/SacI-digested pSGI-YC3. Plasmid pSGI-BL24 contains the L. lactis KDCa and codon-modified S. cerevisiae ADH2 genes as represented in SEQ ID NO:2 and was made by inserting a SpeI/SacI fragment from plasmid pSGI-BL19 into SpeI/SacJ-digested pSGI-YC3.

Synechocystis PCC 6803 cells were transformed with plasmids pSGI-BL7, pSGI-BL22, and pSGI-BL23 as described by Zang et al. (Microbiology 45:241-245). Both recombinant and wild-type control strains were pre-cultivated in 20 mL of BG-11 medium to mid-log phase ($OD_{730\ nm}$=0.7-0.9) on a rotary shaker (150 rpm) at 30° C. with constant illumination (30 µEinsteins $m^{-2}\ sec^{-1}$). Mid-log phase cultures were inoculated in BG-11 containing 1 mM IPTG to obtain 40 mL of culture having an initial culture $OD_{730\ nm}$ of 0.3-0.4). Cultivation was performed under the same conditions as pre-cultivation. Kanamycin (5 µ/ml) was included in recombinant cultures as appropriate. Four mL of culture were collected every 48 hours and centrifuged at 6,000 g for 10 min. Culture supernatants were transferred into clean 1.5 mL microfuge tubes for gas chromatographic analysis as described in Example 1.

Results indicating the levels of 2-methyl-1-butanol, 3-methyl-1-butanol, and isobutanol present in *Synechocystis* PCC 6803 cultures 144 hours after culture inoculation are shown in Table 2.

TABLE 2

Branched-Chain Alcohol Production (in µM) in *Synechocystis* sp. PCC 6803.

| | Wild type PCC 6803 | pSGI-BL7 (PDCl/ ADH2) | pSGI-BL24 (KDCa/ ADH2) | pSGI-BL22 (PDCl/ ADH6) | pSGI-BL23 (KDCa/ ADH6) |
|---|---|---|---|---|---|
| 2-Methyl-1-Butanol | ND | ND | ND | ND | 28 |
| 3-Methyl-1-Butanol | ND | ND | ND | ND | 43 |
| Isobutanol | ND | ND | 10.1 | ND | 188 |

Note:
ND indicates "not detected" (<5uM).
2-Methyl-1-Butanol and 3-Methyl-1-Butanol were identified and quantified by GC-MS. Isobutanol was identified and quantified by GC-FID.

Example 3

Enhanced Production of Branched-Chain Alcohols in Strains of *Synechocystis* sp. by Overexpression of an Acetolactate Synthase Gene A 1.6-kbp DNA fragment comprising the coding region of the acetolactate synthase gene from *Synechocystis* sp. PCC 6803 (ilvB, Cyanobase gene designation sll1981) was amplified from genomic DNA using PCR with primers ilvB-5 (GTTGCACATGTTAGGGCAAATGAACACCGCAGACC SEQ ID NO:5) and ilvB-3 (CTACGTTAACGACAGAGATCTTTATTCCCAAATTTCACAGGCCA; SEQ ID NO:6). This PCR fragment was digested with the restriction enzyme PciI and BglII and the ilvB gene coding region was then inserted into the expression cassette of pSGI-BL27 between the NcoI site and BglII site to yield pSGI-BL34. The expression cassette comprising the trc promoter, the ilvB coding sequence and the rps14 terminator is provided as SEQ ID NO:7.

The pSGI-BL34 vector was transformed into wild-type *Synechocystis* sp. PCC 6803 to form strain SGC-BL34-1 and into *Synechocystis* sp. strain pSGI-BL23-1 (see Example 2) to form strain SGC-BL23-34-1 according to Zang et al., *J Microbiology* (2007) 45:241-245. Insertion of the ilvB gene expression cassette into the "RS2" recombination site (Aoki, et al., *J. Bacteriol* (1995) 177:5606-5611) through homologous recombination was confirmed by PCR screening of insert and insertion site. The strains were then grown in liquid BG-11 medium and tested for the production of branched-chain alcohols. All liquid medium growth conditions used a rotary shaker (150 rpm) at 30° C. with constant illumination (60 µE·m-2·sec-1). Cultures were inoculated in 25 mL of BG-11 medium containing spectinomycin (10 µg/mL) and/or kanamycin (5 µg/mL) accordingly and grown to a sufficient density (minimal OD730 nm=1.6-2.0). Cultures were then used to inoculate 100 mL BG-11 medium in 250 mL polycarbonate flasks to OD730 nm=0.4-0.5 and incubated overnight. 45 mL of overnight culture at OD730 nm=0.5-0.6 were added to new 250-mL flasks, some of which were induced with 1 mM IPTG. 2 mL samples were taken at 0, 48, 96 and 144 hours post induction and processed as described in Example 2. GC results indicating secreted levels of branched-chain alcohols after 144 hours are shown in Table 3.

TABLE 3

Branched-Chain Alcohol Production (µM) in Strains Derived from *Synechocystis* sp. PCC 6803.

| Strain | Parent | Added Plasmid | Transgenes | 2-MBO | 3-MBO | i-BuOH |
|---|---|---|---|---|---|---|
| SGC-BL34-1 | PCC 6803 | pSGI-BL34 | ilvB | ND | ND | ND |
| SGC-BL23-1 | PCC 6803 | pSGI-BL34 | KDCa + ADH6 | 77.6 | 215.8 | 1040.5 |
| SGC-BL23-34-1 | SGC-BL23-1 | pSGI-BL34 | ilvB + KDCa + ADH6 | 97.4 | 250.7 | 1137.1 |

2-MBO refers to 2-methyl-1-butanol
3-MBO refers to 3-methyl-1-butanol
i-BuOH refers to isobutanol

What is claimed is:

1. A recombinant photosynthetic microorganism comprising at least one heterologous nucleic acid sequence that encodes a branched-chain 2-ketoacid decarboxylase and at least one heterologous nucleic acid sequence that encodes an enzyme selected from the group consisting of a citramalate synthase, a 2-methylmalate dehydratase, a 3-isopropylmalate dehydratase, and a 3-isopropylmalate dehydrogenase, wherein the recombinant photosynthetic microorganism produces 2-methyl-1-butanol.

2. The recombinant photosynthetic microorganism of claim 1, wherein the branched-chain 2-ketoacid decarboxylase is selected from the group consisting of a *Saccharomyces cerevisae* PDC1 gene product, a *Pichia stipitis* PDC1 gene product, a *Saccharomyces cerevisae* PDC5 gene product, a *Saccharomyces cerevisae* PDC6 gene product, a *Saccharomyces cerevisae* ARO10 gene product, a *Saccharomyces cerevisae* THI3 gene product, a *Pichia stipitis* PDC 3-6 Kivd gene product, a *Pichia stipitis* PDC2 gene product, a *Mycobacterium tuberculosis* KDC gene product, a *Lactococcus lactis* KDCa gene product, and a variant or homolog of any thereof.

3. The recombinant photosynthetic microorganism of claim 2, wherein the heterologous nucleic acid sequence encodes *Lactococcus lactis* KDCa gene product or a variant thereof.

4. The recombinant photosynthetic microorganism of claim 3, wherein the heterologous nucleic acid sequence encodes a *Lactococcus lactis* KDCa -S286Y, KDCa S286U, or F381W gene product, or a variant of any thereof.

5. The recombinant photosynthetic microorganism of claim 2, wherein the heterologous nucleic acid sequence encodes a *Pichia stipitis* PDC3-6 gene product or a variant thereof.

6. The recombinant photosynthetic microorganism of claim 2, further comprising a heterologous nucleic acid sequence encoding an alcohol dehydrogenase.

7. The recombinant photosynthetic microorganism of claim 6, wherein alcohol dehydrogenase is a branched-chain alcohol dehydrogenase.

8. The recombinant photosynthetic microorganism of claim 7, wherein the alcohol dehydrogenase is selected from the group consisting of a *Saccharomyces cerevisae* ADH1 gene product, a *Saccharomyces cerevisae* ADH2 gene product, a *Saccharomyces cerevisae* ADH3 gene product, a *Saccharomyces cerevisae* ADH6 gene product, a *Saccharomyces cerevisae* ADH7 gene product, a *Saccharomyces cerevisae* GRE2 gene product, a *Saccharomyces cerevisae* SFA1 gene product, a *Saccharomyces cerevisae* YPR1 gene product, a *Pichia stipitis* AdH3 gene product, a *Pichia stipitis* ADH6 gene product, a *Pichia stipitis* ADH7 gene product, a GRE2 gene product, a *Mycobacterium tuberculosis* ADH1 gene product, a *Mycobacterium tuberculosis* ADH gene product, a *Mycobacterium tuberculosis* ADHb gene product, an *E. coli* yqhD gene product, an *Equus caballus* ADHE gene product, and a variant or homolog of any thereof.

9. The recombinant photosynthetic microorganism of claim 8, wherein the heterologous nucleic acid sequence encodes a *Saccharomyces cerevisae* ADH6 gene product.

10. A recombinant photosynthetic microorganism according to claim 1, wherein the photosynthetic microorganism comprises at least one heterologous nucleic acid sequence that encodes a citramalate synthase.

11. A recombinant photosynthetic microorganism according to claim 1, wherein the recombinant photosynthetic microorganism further comprises at least one heterologous nucleic acid sequence that encodes at least one enzyme selected from the group consisting of an acetolactate synthase, a ketol-acid reductoisomerase, and a dihydroxyacid dehydratase.

12. A recombinant photosynthetic microorganism according to claim 11, wherein the recombinant photosynthetic microorganism comprises at least one heterologous nucleic acid sequence that encodes an acetolactate synthase.

13. A recombinant photosynthetic microorganism according to claim 1, wherein the recombinant photosynthetic microorganism further comprises at least one heterologous nucleic acid sequence that encodes at least one enzyme selected from the group consisting of a homoserine dehydrogenase, a homoserine kinase, a threonine synthase, and a threonine ammonia-lyase.

14. A recombinant photosynthetic microorganism according to claim 13, wherein the recombinant photosynthetic microorganism comprises at least one heterologous nucleic acid sequence that encodes a threonine ammonia-lyase.

15. The recombinant photosynthetic microorganism of claim 1, wherein the photosynthetic microorganism is a eukaryotic microalga.

16. The recombinant photosynthetic microorganism of claim 15, wherein the photosynthetic microorganism is selected from the group consisting of *Achnanthes, Amphiprora, Amphora, Ankistrodesmus, Asteromonas, Bookelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomona, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella,* and *Volvox.*

17. The recombinant photosynthetic microorganism of claim 1, wherein the photosynthetic microorganism is a *cyanobacterium.*

18. The recombinant photosynthetic microorganism of claim 17, wherein the photosynthetic microorganism is selected from the group consisting of *Chamaesiphon, Chroococcus, Cyanobacterium, Cyanobium, Dactylococcopsis, Gloeobacter, Gloeocapsa, Gloeothece, Microcystis, Prochlorococcus, Prochloron, Synechococcus, Synechocystis, Chroococcidiopsis, Cyanocystis, Dermocarpella, Myxosarcina, Pleurocapsis, Stanieria, Xenococcus, Arthrospira, Borzia, Crinalium, Geitlerinema, Halospirulina, Leptolyngbya, Limnothrix, Lyngbya, Microcoleus, Oscillatoria, Planktothrix, Prochlorothrix, Pseudanabaena, Spirulina, Starria, Symploca, Trichodesmium,* and *Tychonema, Anabaena, Anabaenopsis, Aphanizomenon, Calothrix, Cyanospira, Cylindrospermopsis, Cylindrospermum, Nodularia, Nostoc, Chlorogloeopsis, Fischerella, Geitleria, Nostochopsis, Iyengariella, Stigonema, Rivularia, Scytonema,* and *Tol othri.*

19. The recombinant photosynthetic microorganism of claim 18, wherein the photosynthetic microorganism is *Synechococcus* or *Synechocystis.*

20. A method for producing 2-methyl-1-butanol, said method comprising:
    (i) providing a culture medium comprising a carbon source,
    (ii) culturing the recombinant photosynthetic microorganism of claim 1 in said culture medium under photoautotrophic conditions, and
    (iii) recovering 2-methyl-1-butanol from said culture medium.

21. The method of claim 20, wherein the culture medium provides inorganic carbon as substantially the sole carbon source.

22. The method of claim 21, wherein the inorganic carbon in the culture medium is CO2.

23. The method of claim 20, wherein the recombinant photosynthetic further comprises a heterologous nucleic acid sequence encoding an alcohol dehydrogenase.

24. The method of claim 20, wherein the recombinant photosynthetic further comprises a heterologous nucleic acid sequence encoding encodes at least one enzyme selected from the group consisting of an acetolactate synthase, a ketolacid reductoisomerase, and a dihydroxyacid dehydratase.

25. The method of claim 20, wherein said at least one heterologous nucleic acid sequence further encodes one or more gene products selected from the group consisting of a homoserine dehydrogenase gene product, a homoserine kinase gene product, a threonine synthase gene product, and a threonine ammonia-lyase gene product.

\* \* \* \* \*